(12) United States Patent
Nishio et al.

(10) Patent No.: US 7,287,413 B2
(45) Date of Patent: Oct. 30, 2007

(54) GAS SENSOR UNIT AND SENSOR CAP

(75) Inventors: Hisaharu Nishio, Tokai (JP); Takashi Nakao, Kasugai (JP); Kazuhiro Kohzaki, Komaki (JP); Keiichi Adachi, Kani (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 11/271,975

(22) Filed: Nov. 14, 2005

(65) Prior Publication Data

US 2006/0101900 A1 May 18, 2006

(30) Foreign Application Priority Data

Nov. 15, 2004 (JP) .......................... P. 2004-330347

(51) Int. Cl.
*G01N 7/00* (2006.01)

(52) U.S. Cl. ...................... 73/23.31; 73/31.05; 204/424

(58) Field of Classification Search ............... 73/23.31, 73/23.32, 31.05, 31.06; 204/424, 425, 426, 204/427, 428, 429

See application file for complete search history.

(56) References Cited

U.S. PATENT DOCUMENTS

| 4,370,213 | A | 1/1983 | Oki et al. | |
|---|---|---|---|---|
| 6,222,372 | B1 * | 4/2001 | Fukaya et al. | ............... 324/464 |
| 6,383,355 | B1 * | 5/2002 | Miyata | ........................ 204/427 |
| 6,453,723 | B1 * | 9/2002 | Ichikawa et al. | ............. 73/23.2 |
| 6,679,099 | B2 * | 1/2004 | Fujita et al. | .................. 73/23.2 |
| 6,817,224 | B2 * | 11/2004 | Hibino et al. | ............... 73/23.31 |
| 6,843,105 | B1 * | 1/2005 | France | ....................... 73/31.05 |
| 2002/0138967 | A1 | 10/2002 | Hattori et al. | |
| 2005/0029101 | A1 * | 2/2005 | Isomura et al. | ............. 204/428 |

FOREIGN PATENT DOCUMENTS

| JP | 53-95884 | 12/1951 |
|---|---|---|
| JP | 53-95886 | 12/1951 |
| JP | 56-131451 | 3/1955 |
| JP | 11-153570 | 6/1999 |

* cited by examiner

*Primary Examiner*—Michael Cygan
(74) *Attorney, Agent, or Firm*—Sughrue Mion Pllc.

(57) ABSTRACT

A gas sensor unit including a gas sensor and a sensor cap. The gas sensor includes a gas detecting element, an electrode provided on the gas detecting element and a sensor terminal connecting to the electrode for transmitting an output signal from the gas detecting element. The sensor cap is adapted for transmitting the output signal to an external device. The sensor cap includes a cap terminal electrically connecting to the sensor terminal and an enclosing member bonding to the gas sensor so as to form an internal space in cooperation with the gas sensor. The enclosing member includes a communicating hole through which the internal space is in communication with a space outside the gas sensor unit, and the communicating hole is gas-permeably and watertightly closed by a filter member.

26 Claims, 12 Drawing Sheets

GAS SENSOR UNIT AND SENSOR CAP

BACKGROUND OF THE INVENTION

1. Field of the Invention

The present invention relates to a gas sensor unit constituting an assembly of a gas sensor having a gas detecting element and a sensor cap fitted thereon for transmitting an output signal from the gas sensor to an external device, as well as the sensor cap alone.

2. Description of the Related Art

Various types of gas sensors having a gas detecting element have hitherto been proposed. One example is a gas sensor having a gas detecting element formed from an oxygen-ion conductive zirconia ceramic, and which is mounted on an exhaust gas pipe of an internal combustion engine so as to detect the oxygen concentration in the exhaust gas (e.g., Japanese Utility Model Publication No. 53-95884 (published in 1978) and Japanese Utility Model Publication No. 53-95886 (published in 1978)).

3. Problems to be Solved by the Invention

The gas sensors of Japanese Utility Model Publication No. 53-95884 and Japanese Utility Model Publication No. 53-95886 have a bottomed tubular gas detecting element and a tubular sensor terminal for outputting an output signal from the gas detecting element outside the sensor. These gas sensors are formed such that the output signal is transmitted outside the sensor (e.g., to an ECU) through a connection terminal connecting to the sensor terminal, a reference gas (outside air) is introduced to the inside of the gas detecting element through a tubular interior of the sensor terminal, and the tubular interior of the sensor terminal and the inside of the gas detecting element are ventilated.

In this type of gas sensor in which the sensor terminal is connected to the connection terminal to transmit an output signal, there are cases where a sensor cap is required which has a cap-like enclosing member for covering the connection terminal (cap terminal) and the sensor terminal for the purpose of protecting the sensor terminal and connection to the sensor terminal.

With such a sensor cap, there are cases where a communicating hole between the outside and an internal space must be provided to speedily ventilate the internal space of the gas sensor and the sensor cap. The purpose thereof is to introduce a reference gas from outside the sensor and to prevent an abnormal change in reference gas concentration (due to generation gas from a foreign object which has entered the interior of the gas sensor or the interior of the sensor cap), as well as to prevent corrosion and the like of the sensor terminal and the cap terminal.

Meanwhile, there are also cases where, in order to prevent short-circuiting, corrosion and the like of the sensor terminal and the cap terminal due to entry of water droplets and the like into the internal space from outside the sensor, the internal space must be made watertight.

SUMMARY OF THE INVENTION

The present invention has been made in view of the above-described circumstances, and an object thereof is to provide a gas sensor unit and a sensor cap, the gas sensor unit including a gas sensor and a sensor cap having a cap terminal for connecting to the sensor terminal of the gas sensor and having an enclosing member for enclosing, the internal space in cooperation with the gas sensor, the gas sensor unit being gas permeable and watertight between the internal space and space outside the gas sensor unit.

The above object of the present invention has been achieved by providing a gas sensor unit comprising: a gas sensor including a gas detecting element, an electrode provided on the gas detecting element and a sensor terminal connecting to the electrode so as to transmit an output signal from the gas detecting element; and a sensor cap for transmitting the output signal to an external device, the sensor cap including a cap terminal electrically connecting to the sensor terminal and an enclosing member bonding to the gas sensor so as to form an internal space in cooperation with the gas sensor, wherein the enclosing member includes a communicating hole through which the internal space is in communication with space outside the gas sensor unit, and the communicating hole is gas-permeably and watertightly closed by a filter member.

The above object of the present invention has also been achieved by providing a sensor cap adapted for fitting to a gas sensor including a gas detecting element, an electrode provided on the gas detecting element and a sensor terminal connected to the electrode for transmitting an output signal from the gas detecting element to an external device, the sensor cap comprising: a cap terminal for electrically connecting to the sensor terminal; an enclosing member for accommodating the cap terminal therein and adapted to define a cap terminal accommodating space for forming an internal space in cooperation with the gas sensor when the sensor cap is fitted to the gas sensor, the enclosing member having a communicating hole through which the cap terminal accommodating space is in communication with space outside the sensor cap; and a filter member which closes the communicating hole gas-permeably and watertightly.

In the invention, the sensor cap is provided with an enclosing member having a communicating hole and a filter member for closing the communicating hole, wherein the internal space and outside space are closed from each other gas permeably and watertightly. Namely, the filter member in cooperation with the communicating hole provides a watertight yet gas permeable passage.

For this reason, ventilation of the internal space is facilitated while preventing entry of water droplets into the internal space. Accordingly, in the case where air in the internal space is used as a reference gas for the gas sensor, the reference gas can be easily introduced into the internal space from outside the gas sensor unit. In addition, rapid ventilation of the internal space can be effected. Consequently, it is possible to prevent an abnormality in the signal output accompanied by an abnormal change in reference gas concentration due to generation gas from a foreign object which becomes attached to the interior of the gas detecting element, the sensor terminal, the cap terminal, or the interior of the enclosing member. Furthermore, corrosion and the like of the sensor terminal and the cap terminal can be prevented.

The gas detecting element may assume a bottomed tubular shape or a plate-like shape. In addition, known materials can be used to fabricate the gas detecting element depending on the gas to be detected. For instance, in an oxygen sensor, a solid electrolyte material consisting mainly of a zirconia ceramic may be used.

In addition, the gas sensor can include, in addition to the gas detecting element and the sensor terminal, a cylindrical insulating member formed from an insulating material and surrounding the sensor terminal.

The enclosing member of the sensor cap forms an internal space with the gas sensor when the gas sensor and the sensor cap are assembled. For example, the internal space is formed by making close contact between the enclosing member and the outer peripheral surface of the gas detecting element or the outer peripheral surface of the sensor terminal. Alternatively, the internal space can be formed by making close contact between the enclosing member and the cylindrical insulating member surrounding the sensor terminal.

The filter member is gas permeable and water repellent, and closes the communicating hole gas permeably and watertightly. This filter member can be positioned at any of the outer end or the inner end of the communicating hole and the inside of the communicating hole without particular limitation.

In addition, the filter member may assume the shape of a sheet, a tube, a cup, or a pole as required, in correspondence with the way that the communicating hole is to be closed. For instance, the sheet-, tube-, cup-, or pole-shaped filter member may be made of GORTEX (trademark) or the like. On the other hand, the pole-shaped filter member may have a continuous porous structure made of polytetrafluoroethylene (PTFE) in which fine pores are three-dimensionally connected with one another.

More specifically, a sheet-type filter member can be fixed to the outer peripheral surface of the enclosing member so as to cover the outer end of the communicating hole.

Alternatively, a pole-type filter member which is gas permeable at least in the axial direction of the communicating hole can be inserted into the communicating hole.

Furthermore, a filter member including a pipe and a filter sheet which closes at least one of the openings of the pipe can be inserted into the communicating hole.

Furthermore, in the gas sensor unit or the sensor cap according to the invention, at least one of the enclosing member and the filter member is preferably formed from a resilient material, and an inner wall surface of the communicating hole of the enclosing member and an outer surface of the filter member are preferably resiliently and watertightly in contact with one another.

As a result, it is possible to enhance watertightness between the inner wall surface of the communicating hole and the outer surface of the filter member.

The resilient material for forming the enclosing member may comprise a resilient high polymer material. The material is appropriately selected by taking into consideration the heat resistance and resiliency of the enclosing member. Furthermore, if ease of deformation is taken into account, it is preferable to use a high polymer material having rubber elasticity. Specifically, a material such as neoprene rubber, chloroprene rubber, silicone rubber and fluoro rubber is preferably used. In a case where heat resistance is required, fluoro rubber is preferred.

In addition, the resilient material for forming the filter member may be, by way of example, a sponge such as urethane foam.

In addition, in the gas sensor unit or the sensor cap according to the invention, the filter member is preferably formed from a water repellent material that is gas permeable at least in a direction of an axis of the communicating hole. Preferably an outer peripheral surface of the filter member is provided with a close contact portion, and the enclosing member is resilient such that an inner wall surface of the communicating hole is brought into close contact with the close contact portion of the filter.

In the invention, even if exposed to high temperature, thermal expansion of the gas sensor unit or sensor cap is not subject to restriction by a crimping member. As such, a reduction in outside diameter due to plastic deformation hardly occurs, thereby preventing a deterioration in watertightness.

In the gas sensor unit or the sensor cap, since the passage of gas (ventilation) can be secured by virtue of the gas permeability of the filter member in the axial direction, and because the close contact portion of the filter member is brought into close contact with the enclosing member without leaving a gap, it is possible to maintain watertightness at the interface between the enclosing member and the filter member. In addition the enclosing member holds the filter member by the resiliency of the enclosing member so that the difference between the thermal expansion rate of the filter member and the enclosing member can be absorbed. For this reason, the filter member can be held and kept watertightly in the communicating hole using a simple structure.

The enclosing member is preferably formed from a resilient high polymer material, which can be selected by taking into consideration such factors as the heat resistance and resiliency of the enclosing member. In view of deformability, it is preferable to use a high polymer material having rubber elasticity. Specifically, it is preferable to use a material such as neoprene rubber, chloroprene rubber, silicone rubber, and fluoro rubber. In a case where heat resistance is required, fluoro rubber is particularly preferred.

Furthermore, in the gas sensor unit or the sensor cap according to the invention, the inner wall surface of the communicating hole of the enclosing member preferably includes an annular protruding portion (1023*m*, 1023*n*, 1123*m*, 1123*n*) protruding inwardly and in close contact with a portion of the close contact portion (1045*b*) of the filter member In a preferred embodiment, the whole of the inner wall surface of the communicating hole is not brought into close contact with the close contact portion of the filter member, but only the annular protruding portion of the inner wall surface is brought into close contact with a portion of the close contact portion. As a result, it is possible to enhance the closely contacting force between the inner wall surface defining the communicating hole and the close contact portion, making it possible to enhance the watertightness therebetween.

Furthermore, in the sensor cap, in order to keep the filter member in the communicating hole (i.e., in order to prevent the filter member from coming out of the communicating hole to the outside), the communicating hole preferably includes a holding portion, e.g., having a smaller diameter than the outer diameter of the filter member.

Furthermore, in the gas sensor unit or the sensor cap of the invention, the sensor cap preferably has a lead wire connecting to the cap terminal for transmitting the output signal to the external device, and the filter member includes an inserting hole which extends through and along, the axis of the communicating hole and in which the lead wire is watertightly held.

In the gas sensor unit of the invention, the filter member preferably includes an inserting hole, and the lead wire is held watertightly in the filter member. This arrangement allows for ventilation between the outside and the internal space through the communicating hole of the enclosing member, and the lead wire can be watertightly led out to the outside through the communicating hole.

For this reason, in a preferred embodiment, it is unnecessary to separately provide the enclosing member with an insertion hole for leading the lead wire to the outside, to hold the lead wire in this insertion hole while inserting the lead wire therethrough, and to separately provide a structure for establishing watertightness between the lead wire and the enclosing member at this portion. Accordingly, it, is possible to provide a gas sensor unit which is simple in structure and is inexpensive.

A technique for holding the lead wire by the filter member includes one in which a crimping member is fitted over a portion (crimping portion) different from the close contact portion in the axial direction and surrounding the inserting hole in the columnar filter member. This portion is crimped, to thereby cause the crimping portion and the inserting hole inside the crimping portion to shrink in diameter, thereby holding the lead wire by the crimping portion. In this case, if the lead wire is to be watertightly held in the filter member, it is possible to cite, for example, a technique of crimping with such strength as to obtain watertightness in fitting the crimping member over the crimping portion and crimping the same, and a technique in which a seal material such as an adhesive is separately provided between the lead wire and the outer surface of the filter member or the inner wall surface of the inserting hole.

In addition, a technique of holding the lead wire includes using an adhesive to secure the lead wire to the inner wall surface of the inserting hole or to the outer surface of the filter member. In this case, to allow the lead wire to be watertightly held in the filter member, it is sufficient if consideration is given to the amount and place of application of the adhesive so as to provide watertightness.

However, in the case where the lead wire is held in the inserting hole by crimping the crimping portion via the crimping member, there are cases where, depending on the extent of shrinkage in diameter of the crimping portion, the gas permeability at this crimping portion in the axial direction becomes insufficient, or gas permeability is lost.

Accordingly, in the case where the lead wire is held in the inserting hole by crimping the crimping portion via a crimping member, it suffices if consideration is given to the form of the filter member or the direction of passage of gas such that a vent passage enabling the passage of gas between the outside and the internal space other than the crimping portion is provided.

For example, it suffices if the filter member which is gas permeable in the axial direction of the communicating hole has a shape in which, in addition to the close contact portion of a relatively large diameter, a small-diameter portion having a smaller diameter than the close contact portion is provided at a position different from the close contact portion in the axial direction. In a filter member of this form, even if the small-diameter portion or a portion offset from the small-diameter portion more distantly from the close contact portion is crimped, the passage of gas is still possible between the surface produced by the difference in diameter between the close contact portion and the small-diameter portion (specifically, an annular surface perpendicular to the axis, or a tapered surface) and the surface of the contact portion on the opposite side of the small-diameter portion. Accordingly, if the filter member is provided in the communicating hole of the enclosing member such that one of these surfaces faces the outside and the other one faces the internal space, it is possible to ensure gas permeability irrespective of the presence or relative permeability of the crimping portion.

Alternatively, it is possible to use a filter member which is gas permeable in the axial direction of the communicating hole, and in which an intermediate gas permeable portion is provided between the close contact portion and the crimping portion, and gas permeability is provided at least at this intermediate gas permeable portion through its outer peripheral surface. In this filter member, even if the crimping portion is crimped, since gas permeability is provided between the outer side of the outer peripheral surface of the intermediate gas permeable portion and the interior of the close contact portion, the passage of gas is possible between the outer peripheral surface of the intermediate gas permeable portion and the surface of the close contact portion on the opposite side of the crimping portion (intermediate gas permeable portion). Accordingly, if the filter member is provided in the communicating hole of the enclosing member such that one of these surfaces faces the outside and the other faces the internal space, it is possible to ensure gas permeability irrespective of the presence or relative permeability of the crimping portion.

Furthermore, in the gas sensor unit or the sensor cap, the filter member preferably includes a close contact portion provided at an outer peripheral surface of the filter member and a crimping portion provided at a position different from the close contact portion in the direction of the axis and having a smaller outer diameter than that of the close contact portion, wherein the sensor cap preferably further includes a crimping member which crimps around the crimping portion of the filter member so that the lead wire is watertightly held in the inserting hole.

In a preferred embodiment of the invention, the filter member includes a crimping portion. Further, the crimping member is fitted over the crimping portion, and the lead wire is watertightly held in the inserting hole. For this reason, it is possible to transmit an output signal to the external device through the lead wire, and it is possible to prevent entry of water into the internal space through the gap between the outer peripheral surface of the lead wire and the inner peripheral surface of the inserting hole of the filter member.

Furthermore, the filter member is gas permeable at least in the axial direction of the communicating hole, and has a close contact portion and a crimping portion of smaller diameter. For this reason, since the small-diameter crimping portion is crimped by the crimping member, even if the gas permeability declines or is lost at this crimping portion, gas permeability is maintained at least between the surface defined by the difference in diameter between the large-diameter close contact portion and the small-diameter crimping portion and the surface of the close contact portion on the opposite side of the crimping portion.

Thus, in the gas sensor unit or the sensor cap of this preferred embodiment, despite the fact that the lead wire is inserted in the filter member, watertightness can be achieved between the filter member and the enclosing member and between the filter member and the lead wire, thereby making it possible to prevent entry of water into the internal space.

Furthermore, in the gas sensor unit or the sensor cap, the communicating hole preferably includes a plurality of openings which are provided between the filter member and the outside, and the filter member is positioned out of sight from outside the gas sensor unit or sensor cap through any of the plurality of openings.

In recent years, as an apparatus for cleaning of automobiles and the like, high-pressure cleaning apparatuses have become widespread which jet pressurized water from a nozzle at high speed. For this reason, in a case where a gas sensor unit in which the filter member is installed in a vehicle at a position where the filter member can be visually confirmed from the outside through the opening of the communicating hole, and the vehicle is washed using a high-pressure cleaning apparatus, the high-speed water may directly reach the filter member. As such, water pressure exceeding the water pressure resistance of the filter member can be applied to the filter member, causing water droplets to undesirably permeate the filter member.

In contrast, in the gas sensor unit or the sensor cap of a preferred embodiment of the invention, the filter member is provided at a position where it cannot be seen directly from the outside through any of the openings. For this reason, the speed of water entering at high speed from the outside through the openings is reduced before it reaches the filter member due to collision against an inner wall surface defining the communicating hole. Accordingly, even in cases where water enters at high speed from the outside through openings of the communicating hole, it is possible to prevent the water from infiltrating the filter member.

Furthermore, even if the filter member is provided at a position where it cannot be visually confirmed from the outside through the opening, in a case where only one opening is provided, if the water continues to enter from the opening at high speed, the inside of the communicating hole is eventually filled with water. If the water enters from the opening at high speed in this state, there is a possibility that water pressure equivalent to the case in which high-speed water directly reaches the filter member will be applied to the filter member, causing water droplets to infiltrate the filter member.

In contrast, in the gas sensor unit or the sensor cap of a preferred embodiment of the invention, a plurality of openings are provided in the communicating hole. As a result, even if water enters from one opening at high speed, the water can be discharged to the outside from the other openings, so that there is no risk of high water pressure being applied to the filter member, making it possible to overcome the above-described malfunction.

For the above-described reason, with the gas sensor unit or the sensor cap of a preferred embodiment of the invention, even in a case where water has entered from the outside through openings of the communicating hole at high speed, it is possible to prevent the water from infiltrating the filter member.

Furthermore, in the gas sensor unit or the sensor cap, the gas sensor detects a gas by measuring a difference in potential that is developed when a reference gas is introduced into the internal space from outside the gas sensor unit through the communicating hole. A vent passage for introducing the reference gas to the gas detecting element is provided between the filter member and the gas detecting element.

Due to the vent passage, it is possible to appropriately detect a gas subject to detection by making use of the reference gas introduced from outside the gas sensor unit.

Furthermore, in the gas sensor unit or the sensor cap, when a direction of movement of the gas sensor when the sensor cap and the gas sensor are assembled is taken as a first moving direction, the cap terminal includes an inner vent passage extending in the first moving direction which is a part of the vent passage and an end portion provided on a side opposite side the gas sensor in the first moving direction. The end portion includes a contact portion abutting an inner surface of the enclosing member in the first moving direction and a non-contact portion spaced apart from the inner surface of the enclosing member so that the reference gas is introduced into the inner vent passage through a gap between the non-contact portion of the cap terminal and the inner surface of the enclosing member.

With the gas sensor unit or the sensor cap in accordance with the invention, due to the contact portion which abuts the inner surface of the enclosing member in the first moving direction, even if subject to vibration or the like, the cap terminal can be reliably prevented from moving in the first moving direction.

Moreover, the non-contact portion spaced apart from the inner surface of the enclosing member allows the reference gas supplied through the communicating hole to be introduced into the inner vent passage through the gap between the non-contact portion of the cap terminal and the inner surface of the enclosing member. Accordingly, with the gas sensor unit of a preferred embodiment of the invention, the reference gas can be led appropriately to the gas detecting element via the tubular portion.

The inner vent passage can be formed in a tubular portion of the cap terminal.

BRIEF DESCRIPTION OF THE DRAWINGS

FIGS. 4A and 4B are diagrams illustrating a cap terminal for use in the sensor cap in accordance with the first embodiment, in which FIG. 4A is a front view, and FIG. 4B is a bottom view;

FIGS. 6A to 6C are partial cross-sectional views illustrating characteristic features of the sensor cap in accordance with first, second, and third modifications, in which FIG. 6A is a partial cross-sectional view of the first modification, FIG. 6B is a partial cross-sectional view of the second modification, and FIG. 6A is a partial cross-sectional view of the third modification;

DESCRIPTION OF REFERENCE NUMERALS

Figure 1:
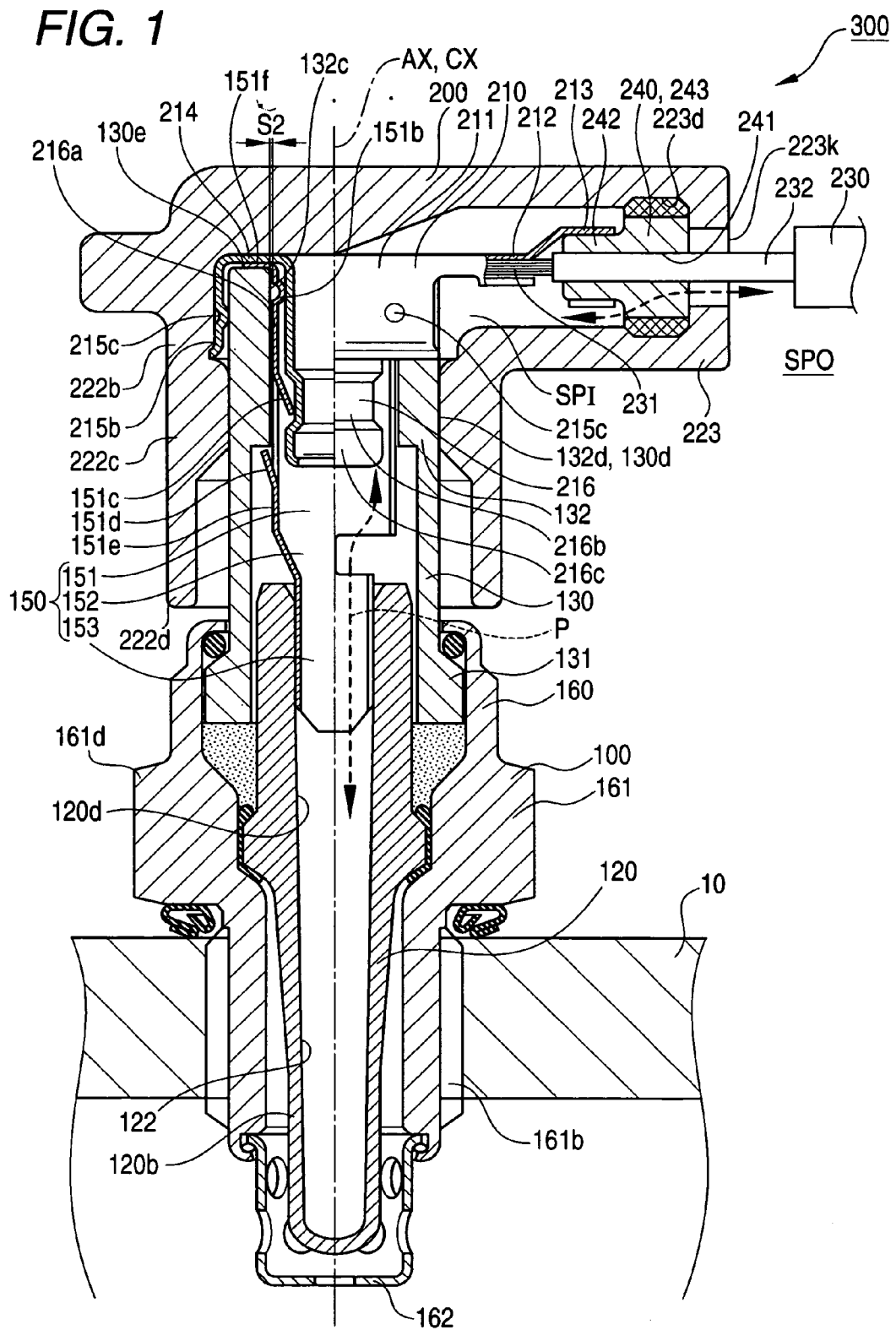
FIG. 1 is an explanatory diagram illustrating a gas sensor unit 300 in accordance with a first embodiment and the manner in which this gas sensor unit is put to use.

Reference numerals used to identify various structural features in the drawings include the following:
AX: axis (of a gas sensor)
100: gas sensor
120: gas detecting element
130: cylindrical insulating member
130d: outer peripheral surface
150: sensor terminal
151: output side terminal portion
153: element-side terminal portion 161: metal shell
200, 400, 500, 600, 700, 1000, 1100: sensor caps
210, 410, 510, 610, 710, 1010: cap terminals
211, 1011: sensor connecting portion (tubular portion)
213, 413, 513: filter crimping portion (crimping member)
613: crimping member
214, 1014: annular end portions (end portions)
215: outer tubular portion (holding portion)
215$b$, 215$ba$, 215$bb$, 215$bc$: resilient end portions
215$c$, 215$ca$, 215$cb$, 215$cc$: projections
215$d$: distal side end (of the outer tubular portion)
SL1, SL2: dividing slits
SL3: dividing slit
216: inner tubular portion
216$a$: conductive portion
220, 420, 520, 620, 720, 1020, 1120: enclosing members
222: joint portion
222$b$: grip portion
222$c$: inner protruding portion
223, 423, 523, 623, 723: lead enclosing portion
223$c$, 423$c$, 523$c$, 623$c$, 723$c$: filter holding hole
223$d$, 423$d$, 523$d$, 623$d$, 723$d$, 1023$d$, 1123$d$: communicating holes
230: lead wire
240, 440, 540, 640, 740, 1040: filter members (filter members)
241, 441, 541, 641, 741: inserting holes
LX: axis (of the inserting hole)
242, 442, 5427 642: crimping portions
242$b$: inner wall surface (of the crimping portion)
243, 443, 543, 643, 743: main bodies
243$b$: outer peripheral surface (of the main body)
243$c$: center portion (of the main body)
243$d$, 443$d$, 543$d$, 743$d$, 1042: outer peripheral close contact portions (of the main bodies)
245: outer protruding portion
250: untreated filter member
253: untreated large-diameter portion
750: bonding seal material
300, 1200: gas sensor units
SPI: internal space
SPO: external space (outside)
SPS: cap terminal accommodating space
1023$n$, 1023$n$, 1123$m$, 1123$n$: annular protruding portions
223$g$, 423$g$, 523$g$, 623$g$, 723$g$, 1023$g$, 1123$g$: holding portions
223$k$, 1023$k$, 1123$kh$, 1123$ki$: openings
214$b$, 1014$b$: contact portions
214$c$, 1014$c$: non-contact portions

DETAILED DESCRIPTION OF THE INVENTION

With reference to the accompanying drawings, a detailed description of preferred embodiments of the invention is given below. However, the present invention should not be construed as being limited thereto,

First Embodiment

Figure 2:
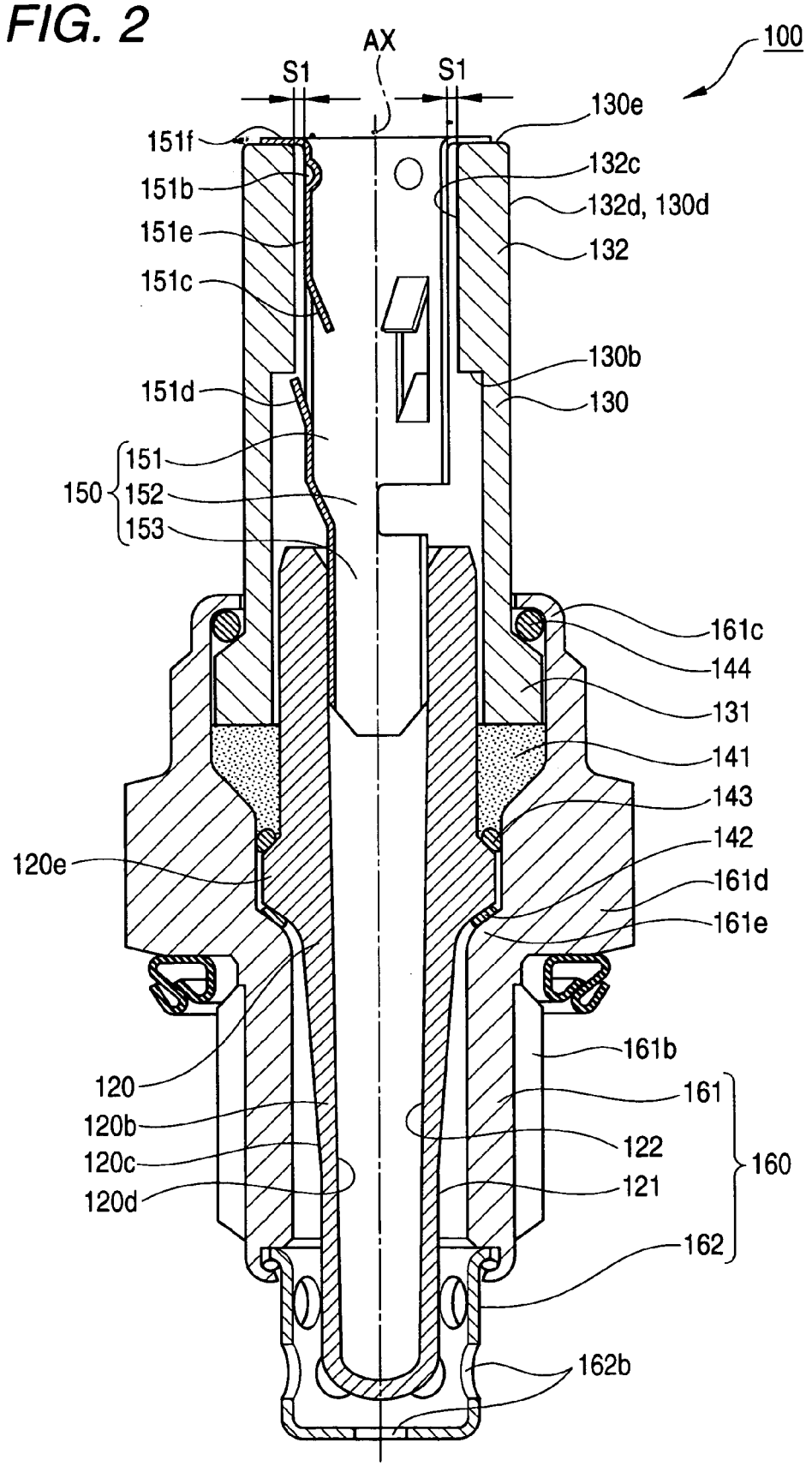
FIG. 2 is a partial cross-sectional view of a gas sensor 100 in accordance with the first embodiment.

FIG. 1 is an explanatory diagram illustrating a gas sensor unit 300 in accordance with a first embodiment and the manner in which this gas sensor unit is put to use. As can be appreciated from FIG. 1, the gas sensor unit 300 in accordance with the first embodiment is comprised of a gas sensor 100 and a sensor cap 200 provided on a rear end side (upper side in FIG. 1) in the direction of an axis AX of this gas sensor 100. This gas sensor unit 300 is an oxygen sensor in which an end portion of the gas sensor 100 is fastened to an exhaust pipe 10 of a vehicle so as to protrude into the exhaust pipe. The gas sensor 100 measures the oxygen concentration of the exhaust gas, As shown in FIG. 2, the gas sensor 100 has a gas detecting element 120, a cylindrical insulating member 130, a sensor terminal 150, and a casing 160.

In the following description, in terms of the direction along the axis AX, the side where the sensor cap is fitted is the rear end side, and the side opposite thereto is the front side.

The casing 160 has a metal shell 161 and a protector 162. The metal shell 161 is made of SUS430 and is formed into a hollow cylindrical shape. A taper-shaped inner-periphery receiving portion 161$e$, whose diameter is reduced toward the front side (lower side in FIG. 2) for supporting a collar 120$e$ of the gas detecting element 120 which will be described below, is provided circumferentially in metal shell 161 so as to protrude from an inner peripheral surface toward the radially inward side. In addition, a threaded portion 161$b$ for fitting the gas sensor 100 to the exhaust pipe 10 (see FIG. 1) is formed on the outer side of the metal shell 161. A hexagonal portion 161$d$, for threadedly inserting the threaded portion 161$b$ into the exhaust pipe 10 using an installation tool, is circumferentially provided on the rear end side (upper side in FIG. 2) of the threaded portion 161$b$. The protector 162 is a bottomed cylindrical member made from a metal, and has a plurality of vent holes 162$b$ for introducing exhaust gas in the exhaust pipe 10 into the interior of the gas sensor 100.

The gas detecting element 120 is formed from an oxygen-ion conductive solid electrolyte, and has a bottomed hollow cylindrical shape in which an end portion 120$b$ is closed and which extends in the direction of the axis AX. The collar 120$e$ protruding radially outwardly is provided on an outer periphery of the gas detecting element 120. The gas detecting element 120 is provided in the metal shell 161 and metallic packing 142 is interposed between a distal end-side face of the collar 120$e$ and the surface of the inner-periphery receiving portion 161$e$ of the metal shell 161. The oxygen-ion conductive solid is typically $ZrO_2$ in which $Y_2O_3$ or $CaO$ is occluded, but a solid solution of $ZrO_2$ and another alkali earth metal or rare earth metal may be used. Further, $HfO_2$ may be contained therein. Known solid electrolytes which are oxygen-ion conductive at high temperature may be used without particular limitation.

An outer electrode 121 is formed at the end portion 120$b$ of this gas detecting element 120 so as to cover its outer peripheral surface 120$c$. Outer electrode 121 is formed into a porous state from Pt or a Pt alloy. This outer electrode 121 is provided up to a distal end-side surface of the collar 120$e$, and electrically connects to the metal shell 161 through the metallic packing 142. For this reason, the potential of the outer electrode 121 can be measured at the metal shell 161.

Meanwhile, an inner electrode 122 is formed on an inner peripheral surface 120$d$ of the gas detecting element 120 so as to cover the inner peripheral surface 120$d$. This inner electrode 122 is also formed into a porous state from Pt or a Pt alloy.

The cylindrical insulating member 130 is made from an insulating ceramic (specifically alumina) and has a hollow cylindrical shape. This cylindrical insulating member 130 is held such that its distal end-side portion 131 having an enlarged thickness, together with a ceramic powder 141 formed from talc, is interposed between the gas detecting element 120 and the metal shell 161 so as to surround a periphery of that portion of the gas detecting element 120 provided on the rear end side of the collar 120*e*.

The sensor terminal 150 made from, for example, SUS304, is tubular, and has an output-side terminal portion 151, an element-side terminal portion 153, and a connecting portion 152 connecting both portions.

Figure 4A:
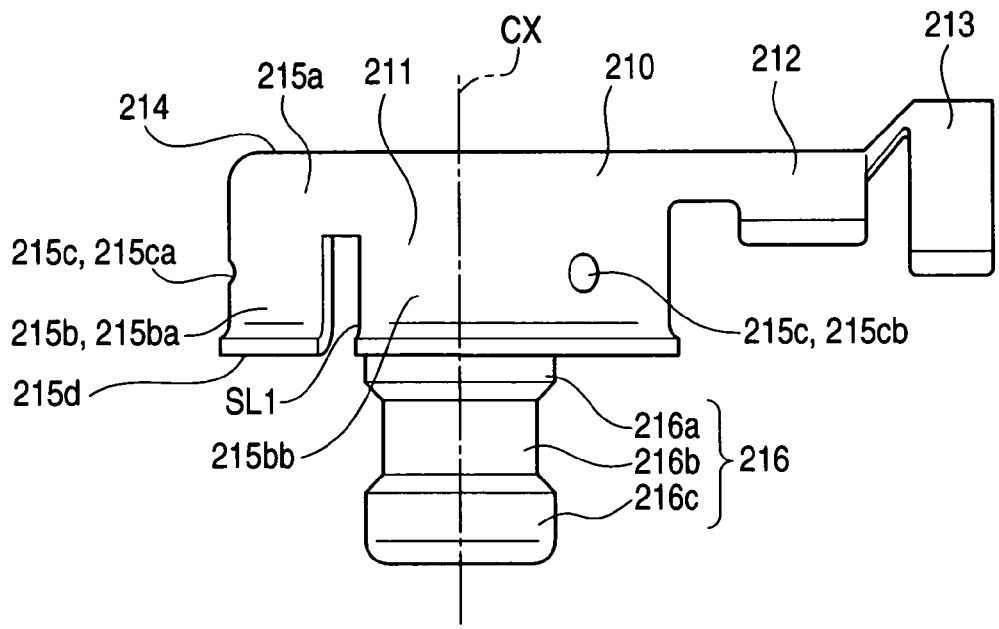
Figure 4B:
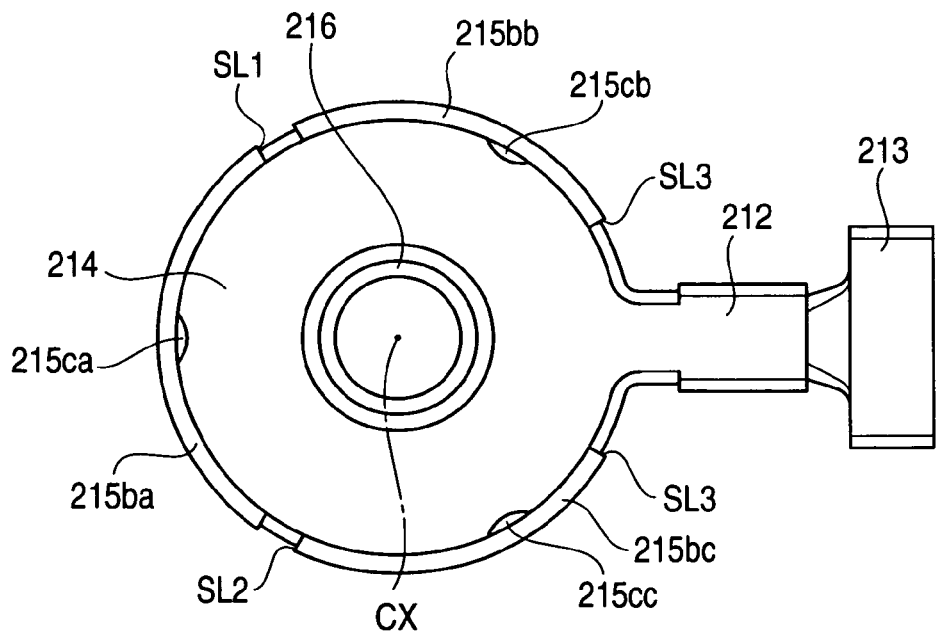

Of these portions, the output-side terminal portion 151 has a tubular shape which is formed substantially in the shape of the letter C in terms of its cross section perpendicular to the axis AX. The output side terminal portion 151 is arranged to resiliently expand in diameter when a sensor connecting portion 211 (see FIGS. 1 and 4) of a cap terminal 210 is inserted into the inside of the output side terminal portion 151 by relatively moving the cap terminal 210 in a direction along the axis AX (vertically in FIGS. 1 and 2). Further, protruding portions 151*b* which protrude radially inwardly are formed at three circumferential portions on the rear end side (upper side in FIG. 2) of the output side terminal portion 151.

Further, in the output side terminal portion 151, inwardly bent portions 151*c* bent radially inwardly by stamping portions of the output side terminal portion 151 and outwardly bent portions 151*d* bent radially outwardly are respectively formed at three corresponding circumferential portions on the front side (lower side in FIG. 2) of the protruding portions 151*b*. Of these portions, each inwardly bent portion 151*c* is formed such that when an inner tubular portion 216 (see FIGS. 4A and 4B) of the cap terminal 210 is inserted into the output side terminal portion 151 so as to connect thereto, as will be described below, the inwardly bent portion 151*c* is resiliently bent radially outwardly. Also, when the inner tubular portion 216 is inserted up to a predetermined position, its bend is returned to produce a clicking sense. In addition, when this sensor terminal 150 is mounted to the gas sensor 100, as shown in FIG. 2, the outwardly bent portions 151*d* abut a distal end face (stepped surface) of the cylindrical insulating member 130, so as to prevent the output side terminal portion 151 (sensor terminal 150) from coming off.

On the other hand, in the sensor terminal 150, the element-side terminal portion 153 has a tubular shape which is formed substantially in the shape of the letter C in terms of its cross section perpendicular to the axis AX. As shown in FIG. 2, this element-side terminal portion 153 is inserted into the gas detecting element 120 while resiliently shrinking in diameter, and electrically connects to the inner electrode 122. Accordingly, in the gas sensor 100 of the first embodiment, the element-side terminal portion 153 electrically connects to the inner electrode 122 while pressing the inner electrode 122 from the inner side toward the radially outer side.

The sensor terminal 150 is integrally formed by press working using a single metal plate of a predetermined shape. For this reason, forming is facilitated, and the production cost is low. In addition, in the sensor terminal 150 of the first embodiment, since the output side terminal portion 151 and the element-side terminal portion 153 provided on the front side thereof in the direction of the axis (lower side in FIG. 2) are formed in a tubular shape by bending a metal plate, it is possible to secure a vent passage P (indicated by the broken-line arrows in FIG. 1) through which a reference gas (outside air) supplied to the sensor cap 200 is introduced to the inside (inner electrode 122) of the gas detecting element 120.

The above-described gas sensor 100 is manufactured as follows.

First, as shown in FIG. 2, the casing 160 in which the metal shell 161 and the protector 162 are integrated is prepared. Then, the gas detecting element 120 provided with the outer electrode 121 and the inner electrode 122, together with the packing 142, is inserted into the casing 160. A ring packing 143 is then provided on the rear end side of the collar 120*e* of the gas detecting element 120, and a predetermined amount of ceramic powder 141 is filled into the gap portion between the metal shell 161 and the gas detecting element 120. Subsequently, the cylindrical insulating member 130 is inserted such that its distal end-side portion 131 is interposed between the gas detecting element 120 and the metal shell 161 to abut the ceramic powder 141. The cylindrical insulating member 130 is then pressurized toward the front side, and under the pressurized state a crimp ring 144 is interposed between a crimp portion 161*c* of the metal shell 161 and the cylindrical insulating member 130, and the crimp portion 161*c* is crimped, thereby integrally fixing the aforementioned component parts.

Finally, the sensor terminal 150 is inserted into the cylindrical insulating member 130 and the gas detecting element 120. Specifically, the element-side terminal portion 153 of the sensor terminal 150 is inserted into the gas detecting element 120 while resiliently shrinking in diameter, and electrically connects to the inner electrode 122. In conjunction with this step, the output side terminal portion 151 is pressed in toward the front side to allow a stopper portion 151*f* formed in the shape of petals oriented radially outwardly perpendicularly to the axis AX to abut a rear end face 130*e* of the cylindrical insulating member 130 from the rear end of the output side terminal portion 151. Thus, the output side terminal portion 151 is provided on the inner side of the cylindrical insulating member 130.

It should be noted that as the output side terminal portion 151 is pressed in until the stopper portion 151*f* abuts against the rear end face 130*e* of the cylindrical insulating member 130, the outwardly bent portions 151*d* bent radially inwardly are released and return, and engage the distal end face (stepped surface) of the stepped portion 130*b* of the cylindrical insulating member 130. Hence, it is possible to prevent the sensor terminal 150 from coming off.

The gas sensor 100 is thus obtained.

It should be noted that in the state in which the inner tubular portion 216 of the cap terminal 210 is not inserted in the output side terminal portion 151, as shown in FIG. 2, the output side terminal portion 151 is in a state in which its diameter is slightly smaller than the inside diameter of a rear end portion 132 of the cylindrical insulating member 130. For this reason, a gap S1 is produced between an inner peripheral surface 132*c* of the rear end portion 132 of the cylindrical insulating member 130 and an outer peripheral surface 151*e* of the output side terminal portion 151.

Figure 3:
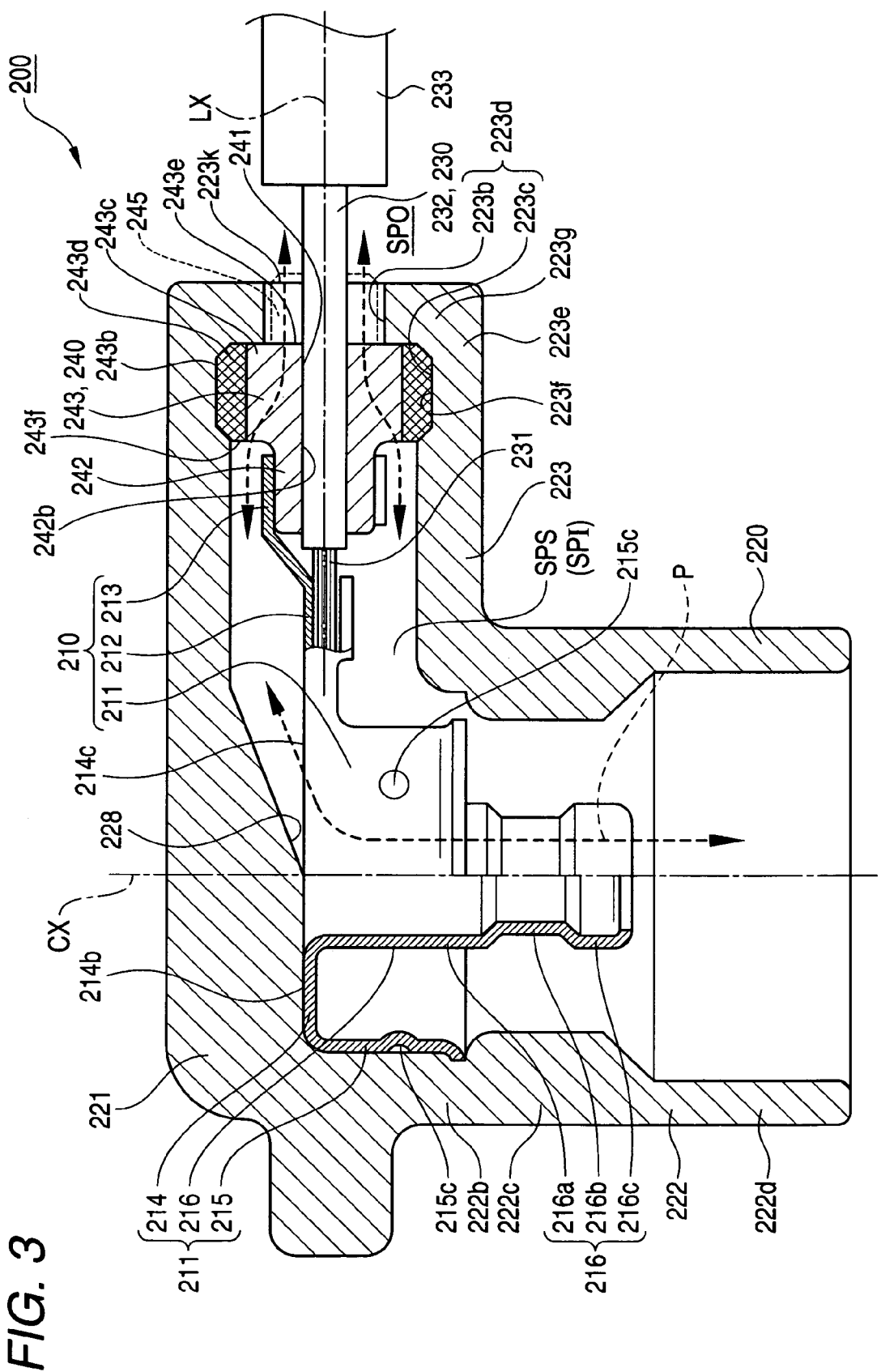
FIG. 3 is a partial cross-sectional view of a sensor cap 200 in accordance with the first embodiment.

Next, the sensor cap 200 of the first embodiment will be described with reference to the drawings. FIG. 3 is a partial fragmentary cross-sectional view of the sensor cap 100. The sensor cap 200 has the cap terminal 210, an enclosing member 220 for covering and holding the cap terminal 210, a lead wire 230, and a filter member 240.

Of these members, the enclosing member 220 is molded into a hollow shape from an insulating fluorine-based rubber, and defines a cap terminal accommodating space SPS for accommodating the cap terminal 210. This enclosing member 220 has a terminal rear end portion 221 provided on the rear end side (upper side in the drawing) of the cap terminal 210; a joint portion 222 for enclosing a radial periphery of the cap terminal 210 and for enclosing an outer peripheral surface of the cylindrical insulating member 130 of the gas sensor 100, as will be described below; and a lead enclosing portion 223 for enclosing the lead wire 230 or a periphery of the filter member 240. The lead wire 230 is led into the enclosing member 220 through a communicating hole 223d consisting of a small-diameter vent hole 223b and a filter holding hole 223c.

In the joint portion 222, a grip portion 222b on the rear end side (upper side in the drawing) is made large in diameter, and is provided around an outer tubular portion 215 of the cap terminal 210. An inner protruding portion 222c, whose diameter is smaller than this grip portion 222b and which has a size for coming into close contact with an outer peripheral surface 130d (outer peripheral surface 132d of the rear end portion 132) of the cylindrical insulating member 130 of the gas sensor 100, is provided on the front side (lower side in the drawing) adjacent to the grip portion 222b. Further, a guide portion 222d, whose diameter is made larger than the inner protruding portion 222c and which extends from the inner protruding portion 222c toward the front side so as to surround the outer peripheral surface 130d of the cylindrical insulating member 130 of the gas sensor 100 in a spaced-apart relation thereto, is provided on the front side (lower side in the drawing) of the inner protruding portion 222c.

The cap terminal 210 (see FIGS. 3 and 4) is made from, for example, INCONEL 718 (trademark of Inco Alloys International, Inc.), and may be formed, for example, by drawing a plate. The cap terminal 210 has a sensor connecting portion 211 of a double substantially cylindrical shape, as well as a core crimping portion 212 formed integrally with the sensor connecting portion 211 so as to electrically connect to a core wire 231 of the lead wire 230 by crimping. Further, the cap terminal 210 has a filter crimping portion 213 for gripping and fixing the lead wire 230 and the filter member 240 by crimping the filter member 240 with the lead wire 230 inserted therein, as will be described below.

Of these portions, the sensor connecting portion 211 has an annular end portion 214 which is annularly concentric with an axis CX; the outer tubular portion 215 which extends toward along the axis CX; and a hollow cylindrical inner tubular portion 216 which extends toward the same direction as the outer tubular portion 215, substantially parallel to the outer tubular portion 215. The annular end portion 214, the outer tubular portion 215, and the inner tubular portion 216 are integrally formed with one another.

Of these portions, the outer tubular portion 215 has a proximal end portion 215a provided adjacent to the annular end portion 214 and resilient end portions 215b (215ba, 215bb, and 215bc) which extend from this proximal end portion 215a by being divided into three parts by slits SL1 and SL2. Further, third slits SL3 are respectively present at both circumferential ends of the proximal end portion 215a. The slits SL1, SL2, and SL3 extend from a distal side end 215d of the outer tubular portion 215 towards the proximal end portion 215a.

Projections 215c (215ca, 215cb, and 215cc) which protrude inwardly are positioned respectively corresponding to the aforementioned resilient end portions 215ba, 215bb, and 215bc. Specifically, the three projections 215ca, 215cb, and 215cc are arranged circumferentially at angles spaced apart by 120° with respect to one another.

As will be described below, the three projections 215c respectively abut the outer peripheral surface 130d (the outer peripheral surface 132d of the rear end portion 132) of the cylindrical insulating member 130 of the gas sensor 100, and the cap terminal 210 is fitted over the cylindrical insulating member 130 such that the outer tubular portion 215 of the sensor connecting portion 211 encloses the rear end portion 132 of the cylindrical insulating member 130. In this case (see FIG. 1), the three resilient end portions 215b respectively are resiliently thrust outwardly due to the presence of the dividing slits SL1, SL2, and SL3. The cap terminal 210 thus resiliently holds the cylindrical insulating member 130 by means of this reaction force.

Meanwhile, the inner tubular portion 216 has a hollow cylindrical shape about the axis CX, as described above, and is rigid to the extent that deformation such as shrinkage and enlargement in diameter hardly occurs. Accordingly, when the inner tubular portion 216 is inserted into the output-side terminal portion 151 of the gas sensor 100 to abut the same, as described below, the inner tubular portion 216 is capable of enlarging the diameter of the output-side terminal portion 151 without undergoing deformation itself.

This inner tubular portion 216 has a conductive portion 216a which has a hollow cylindrical shape with a relatively large diameter and in the general direction of the axis C; a small-diameter portion 216b having a smaller diameter than this conductive portion 216a; and an insertion end portion 216c having a larger diameter than the small-diameter portion 216b.

In the case where the outer tubular portion 215 of the sensor connecting portion 211 is fitted over the cylindrical insulating member 130 of the gas sensor 100 (see Pig. 1), the inner tubular portion 216 is inserted into the inner side of the cylindrical insulating member 130 and the inner side of the output-side terminal portion 151 of the sensor terminal 150. At this juncture, the conductive portion 216a abuts the protruding portions 151b of the output side terminal portion 151, and is in electrical contact with the output side terminal portion 151. Further, the inwardly bent portion 151c of the output side terminal portion 151 is provided on the radially outer side of the small-diameter portion 216b, and when the cap terminal 210 is detached from the sensor terminal 150, this inwardly bent portion 151c is engaged with the insertion end portion 216c so that the cap terminal 210 will not easily come off. Furthermore, when insertion of the inner tubular portion 216 of the cap terminal 210 into the output side terminal portion 151 of the sensor terminal 150 is completed, the inwardly bent portion 151c is disengaged with the insertion end portion 216c, to produce a clicking sense.

It should be noted that in the state in which the inner tubular portion 216 is inserted in the output side terminal portion 151 of the sensor terminal 150 as shown in FIG. 1, the annular end portion 214 abuts the stoppers portion 151f of the output side terminal portion 151 provided on top of the rear end face 130e of the cylindrical insulating member 130, thereby preventing the inner tubular portion 216 of the cap terminal 210 from being further inserted into the front side.

Next, a description will be given of the lead enclosing portion 223 (see FIG. 3). This lead enclosing portion 223 encloses the lead wire 230 and the filter member 240, and includes a filter holding portion 223e and a holding portion 223g for holding the filter member 240 in its interior. The communicating hole 223d consists of the filter holding hole 223c defined by an inner wall surface 223f of the filter holding portion 223e and a small-diameter vent hole 223b defined by an inner wall surface of the holding portion 223g. Communicating hole 223d allows an external space SPO and an internal space SPI (see FIG. 1) formed by the gas sensor 100 and the sensor cap 200 to communicate with one another, and is used to lead in the lead wire 230 from outside the gas sensor unit.

The lead wire 230 has, in addition to the core wire 231, a double covering including a first covering 232 and a second covering 233. The lead wire 230 electrically connects to the sensor connecting portion 211 as the tip of the core wire is crimped by the core crimping portion 212 of the cap terminal 210. In this manner, an output signal from the inner electrode 122 of the gas detecting element 120 of the gas sensor 100 may be transmitted to an external device (e.g., an engine control unit (ECU))

The filter member 240 has an inserting hole 241 in its center, a crimping portion 242 having a relatively small diameter and a main body 243 of a larger diameter than the crimping portion 242. This filter member 240 is formed from PTFE (polytetrafluoroethylene) having a continuous porous structure of continuous fine pores, which material is gas permeable in three-dimensional directions in addition to the direction of an axis LX (left-and-right direction in FIG. 3) of the inserting hole 241.

Of the lead wire 230, the core wire 231 and the first covering 232 are inserted in the inserting hole 241. The crimping portion 242 of the filter member 240 is crimped by the filter crimping portion 213 of the cap terminal 210, as described above, thereby integrating the filter member 140 and the first covering 232 with the cap terminal 210. In addition, the crimping portion 242 of the filter member 240 is firmly crimped by the filter crimping portion 213 so as to be watertight, thereby preventing the entry of water droplets through the inserting hole 241.

The main body 243 of the filter member 240 has a columnar shape extending in the direction of the axis LX, and includes a center portion 243c provided around the inserting hole 241 and a outer peripheral close contact portion 243d which annularly surrounds the periphery of the center portion 243c. In contrast to the center portion 243c which is porous and three-dimensionally gas permeable this outer peripheral close contact portion 243d is dense and is not porous. An outer peripheral surface of this outer peripheral close contact portion 243d has a lower surface roughness than other external surfaces (e.g., gas permeable surface 243e).

The filter member 240 is fixed in place as the main body 243 is clamped by the filter holding portion 223e of the lead enclosing portion 223 by the resiliency of the lead enclosing portion 223. Since the filter member 240 (its main body 243) is held by the resiliency of the lead enclosing portion 223, even if the temperature of this portion becomes high, the filter member 240 is capable of undergoing thermal expansion. Hence, plastic deformation of the filter member 240 (its main body 243) is limited. For this reason, its watertightness is unlikely to deteriorate due to such plastic deformation, so that high reliability with respect to watertightness is secured.

It should be noted that since the outer peripheral surface 243b of the main body 243 is made smooth, as described above, the outer peripheral surface 243b and the inner wall surface 223f of the filter holding portion 223e holding the filter member 240 are brought into closer contact with each other than in the case where a filter member not provided with smoothing treatment is used, so that entry of water from this portion can be prevented more reliably.

In addition, as described above, since the filter member 240 is formed from PTFE having a continuous porous structure, as described above, water droplets can not permeate but air can permeate through the main body 243. Accordingly, in the sensor cap 200 of the first embodiment, as shown by the broken-line arrows in FIGS. 1 and 3, passage of gas can be carried out between the gas permeable surface 243e facing the external space SPO, of the main body 243 of this filter member 240, and a step surface 243f facing the internal space SPI formed by the gas sensor 100 and the sensor cap 200. Accordingly, rapid ventilation of the internal space SPI can be effected. In addition, it is also possible to supply outside air (reference gas) to the inside of the gas detecting element 120 of the gas sensor 100 via the interior of the enclosing member 220 and the interior of the sensor terminal 150.

Further, the lead enclosing portion 223 has, at a position (adjacent on the right side in the drawing) adjacent to the filter holding portion 223e, a holding portion 223g whose diameter is smaller than that of the filter holding portion 223e. The holding portion 223g has a form which juts out inwardly (toward the axis LX side) of the filter holding portion 223e. By virtue of the holding portion 223g which juts out toward the axis LX, the filter member 240 is held in place, namely, the filter member 240 is prevented from coming out of the communicating hole 223d (small-diameter vent hole 223b) to the outside (to the right side in the drawing).

In forming filter member 240, a PTFE powder is charged into a mold of a predetermined shape, and after it is compacted with such compressive force as to produce gaps between the powder particles, the compacted PTFE is heated at a temperature lower than the melting point of PTFE. The powder particles are thereby fused together, forming an untreated filter member 250 (see FIG. 5) of a predetermined shape having a continuous three-dimensional porous structure of microscopically fine pores and which is three-dimensionally gas permeable.

An untreated large-diameter portion 253 of the untreated filter member 250, which is later formed into the main body 243, has a larger diameter than the main body 243.

Figure 5:
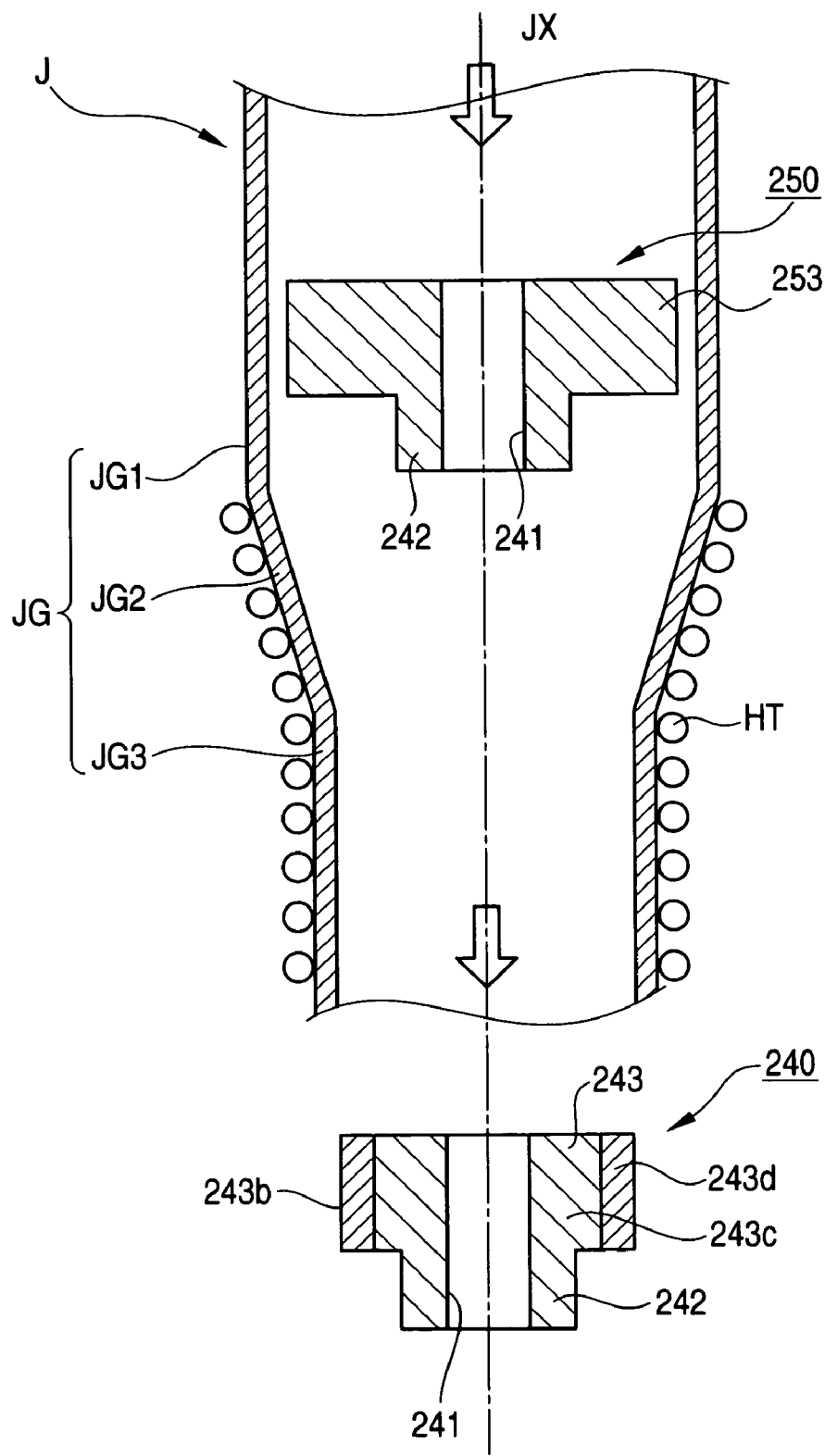
FIG. 5 is an explanatory diagram illustrating smoothing treatment of a main body in a filter member used in the sensor cap in accordance with the first embodiment.

Next, the filter 240 of the first embodiment is formed by using a smoothing apparatus J shown in FIG. 5. The smoothing apparatus J having a center axis JX consists of a smoothing tube member JG and a heater HT. Of these, the smoothing tube member JG has a large-diameter tube portion JG1 of a hollow cylindrical shape whose diameter is larger than the diameter of the untreated large-diameter portion 253 of the untreated filter member 250. Further, the smoothing tube member JG includes a small-diameter tube portion JG3, which has a hollow cylindrical shape with a diameter identical to that of the main body 243 of the filter member 240 after treatment and smaller than that of the large-diameter tube portion JG1, and whose inner peripheral surface is smooth; and a tapered tube portion JG2 which is tapered and connects the large-diameter tube portion JG1 and the small-diameter tube portion JG3. Of these portions, the heater HT is wound around the outer side of the tapered tube portion JG2 and the small-diameter tube portion JG3, so as to be able to heat these portions.

Specifically, the tapered tube portion JG2 and the small-diameter tube portion JG3 are kept in advance at a temperature slightly higher than the melting point of PTFE using the heater HT. After that, the untreated filter member 250 is charged into the large-diameter tube portion JG1, and is pushed in toward the tapered tube portion JG2 and the small-diameter tube portion JG3. Then, as it progresses, the untreated large-diameter portion 253 of the untreated filter member 250 abuts the tapered tube portion JG2, and is pressed toward the inner side. In conjunction with this last step, the outer peripheral portion of the untreated large-diameter portion 253 melts by the heat from the tapered tube portion JG2, and the fine pores are crushed. At the point of time when the filter member is removed from the small-diameter tube portion JG3, the outside diameter of the main body 243 conforms to the inside diameter of the small-diameter tube portion 303, and the outer peripheral close contact portion 243d provided at the outer periphery of the main body 243 becomes a dense and nonpermeable one which consists of once-melted PTFE. In addition, the outer peripheral surface 243b of this outer peripheral close contact portion 243d is made smooth by the inner peripheral surface of the small-diameter tube portion JG3.

Thus, the filter member 240 for use in the first embodiment is formed.

It should be noted that, subsequently, the lead wire 230 is inserted into the inserting hole 241 of this filter member 240, the core wire 231 is crimped by the core crimping portion 212 of the cap terminal 210, and the crimping portion 242 of the filter member 240 is crimped by the filter crimping portion 213. As a result, the first covering 232 of the lead wire 230 is crimped by the crimping portion 242 of the filter member 240 and is watertightly integrated. Subsequently, after the lead wire 230 is passed through the communicating hole 223d (the small-diameter vent hole 223b and the filter holding hole 223c) and is pulled to the outside, the cap terminal 210 is pushed into the enclosing member 220, and the filter member 240 is provided on the inner side of the filter holding hole 223c and is held by the filter holding portion 223e, thereby completing the sensor cap 200.

The manner in which the gas sensor unit 300 consisting of the gas sensor 100 and the gas sensor cap 200 of the first embodiment is put to use is shown in FIG. 1. This gas sensor unit 300 can be used for detecting the oxygen concentration in the exhaust gas of an internal combustion engine, for example.

Specifically, in the gas sensor 100, the front side including the protector 162 is first positioned inside the exhaust pipe 10, and is threadedly secured to the exhaust pipe 10 in a form in which the portion of the metal shell 161 provided on the rear end side of the threaded portion 161b is exposed to the outside. It should be noted that, at this time, the outer electrode 121 which electrically connects to the metal shell 161 is body-grounded through the metal shell 161. Next, with the axis CX of the cap terminal 210 aligned with the axis AX of the gas sensor 100, the sensor cap 200 is moved in a direction along the axes AX and CX (vertical direction in FIG. 1), and the sensor cap 200 is fitted to the gas sensor 100 such that the inner tubular portion 216 of the cap terminal 210 is inserted on the inner side of the output side terminal portion 151 of the gas sensor 100, thereby assembling the gas sensor unit 300. It should be noted that, in this first embodiment, in the direction along the axes AX and CX (vertical direction in FIG. 1), the direction from the gas sensor 100 toward the sensor cap 200 (upward direction in FIG. 1) is designated as a first moving direction.

As shown in FIG. 3, in the sensor connecting portion 211 (corresponding to the tubular portion) of the cap terminal 210, the annular end portion 214 (corresponding to a end portion) provided on a first-moving-direction side (upper side in FIG. 3) has a contact portion 214b abutting an inner surface 228 of the enclosing member 220. Namely, the cap terminal 210 abuts the inner surface 228 of the enclosing member 220 in the first moving direction (upwardly in FIG. 3). For this reason, when the sensor cap 200 is fitted to the gas sensor 100 in the above-described manner, the cap terminal 210 can be connected to the sensor terminal 150 in a state in which movement of the cap terminal 210 in the first moving direction is restricted.

Accordingly, in this first embodiment, when the sensor cap 200 and the gas sensor 100 are assembled, the annular end portion 214 of the cap terminal 210 abuts the stopper portion 151f of the gas sensor 100. Consequently, there is no possibility of the cap terminal 210 becoming positionally offset in the first moving direction. For this reason, if the sensor cap 200 and the gas sensor 100 are joined by abutting the annular end portion 214 of the cap terminal 210 against the stopper portion 151f of the gas sensor 100, the cap terminal 210 and the sensor terminal 150 can be connected appropriately in place.

Moreover, the annular end portion 214 of the cap terminal 210 has a non-contact portion 214c which is spaced apart from the inner surface 228 of the enclosing member 220. Namely, in this first embodiment, the cap terminal accommodating space SPS (internal space SPI) is enlarged between the annular end portion 214 of the cap terminal 210 and the inner surface 228 of the enclosing member 220, thereby allowing a portion of the vent passage P (indicated by the broken-line arrows in FIG. 3) for the reference gas introduced from the outside to be formed between the annular end portion 214 of the cap terminal 210 and the inner surface 228 of the enclosing member 220. For this reason, outside air (reference gas) introduced from the external space SPO through the communicating hole 223d can be introduced into the inner vent passage in the inner tubular portion 216 of the cap terminal 210 through the gap between the non-contact portion 214c of the cap terminal 210 and the inner surface 228 of the enclosing member 220. Accordingly, it becomes possible to efficiently introduce outside air (reference gas) to the inside of the gas detecting element 120 of the gas sensor 100.

In addition, when the sensor cap 200 and the gas sensor 100 are assembled, the rear end-side portion of the outer peripheral surface 130d of the cylindrical insulating member 130 of the gas sensor 100 (outer peripheral surface 132d of the rear end portion 132) is enclosed and directly gripped by the outer tubular portion 215 of the cap terminal 210, as shown in FIG. 1. As a result, the cap terminal 210 is fixed to the cylindrical insulating member 130. Accordingly, the sensor cap 200 is fitted and fixed to the gas sensor 100. In this first embodiment, since the cylindrical insulating member 130 is gripped from the radially outer side by the outer tubular portion 215 of the cap terminal 210, the cap terminal 210 can be reliably fixed. In addition, since the form and size of the outer tubular portion 215 can be determined without being affected by matters related to dimension, the form and dimensions can be easily specified for this outer tubular portion 215 so as to be able to grip the cylindrical insulating member with an appropriate holding force.

In addition, since the cap terminal 210 is fixed to the cylindrical insulating member 130 by the outer tubular portion 215, the other portion, i.e., the inner tubular portion 216 (conductive portion 216a, etc.), is also fixed to the cylindrical insulating member 130.

On the other hand, as for the inner tubular portion 216 of the cap terminal 210, the conductive portion 216a abuts the protruding portions 151b of the output side terminal portion 151. Accordingly, the output side terminal portion 151 at a plurality of (in this first embodiment, three) contact portions electrically connects directly to the conductive portion 216a of the cap terminal 210 while resiliently pressing it radially inwardly. Thus, in this first embodiment, the outer tubular portion 215 at its plurality of contact portions (projections 215c) is in contact with the cap terminal 210. It is therefore possible to minimize the risk of such occurrence as an instant disconnection between the output side terminal portion 151 and the cap terminal 210 and to minimize noise generation (risk of a decline in gas detection accuracy) due to, for example, vibration of the vehicle.

Further, the output side terminal portion 151 at its protruding portions 151b receives a radially outward force from the conductive portion 216a, so that the output side terminal portion 151 is resiliently enlarged in diameter. As the output side terminal portion 151 is thus enlarged in diameter, a gap S2 between the outer peripheral surface 151e of the output side terminal portion 151 and the inner peripheral surface 132c of the rear end portion 132 of the cylindrical insulating member 130 is set to be smaller than the gap S1 before insertion (S2<S1).

However, in a case where the cylindrical insulating member 130, the output side terminal portion 151, and the conductive portion 216a whose dimensions fall within tolerances are used by taking the dimensional tolerances of these portions into consideration, in all cases it is sufficient if a setting is provided such that the gap S2 assumes a value greater than 0 (S2>0). In this case, the size and dimensional tolerances of the output side terminal portion 151 and the conductive portion 216a can be set, as required, such that proper insertion resistance and proper pressure contacting force for continuity can be obtained for the protruding portions 151b and the conductive portion 216a.

It should be noted that even if the gap S2>0, since the cap terminal 210 (conductive portion 216a) is fixed to the cylindrical insulating member 130 by the outer tubular portion 215, even if the gas sensor unit 300 is subject to vibration of the vehicle and the like, the output side terminal portion 151 in a state of being enclosed by the cylindrical insulating member 130 does not swing in the radial direction. For this reason, it is possible to prevent the occurrence of a fatigue failure (fracture, breakage, etc,) in the connecting portion 152 of the sensor terminal 150 and the like due to vibration.

Thus, the gas sensor unit 300 in accordance with the first embodiment presents small risk of such as a decline in gas detection accuracy and breakage of the sensor terminal 150 due to vibration, and its vibration resistance is excellent. Accordingly, the gas sensor unit 300 in accordance with the first embodiment can be suitably used for a two-wheeled vehicle which undergoes intense vibrations.

Further, the cap terminal 210 resiliently connects to the outer peripheral surface 130d of the cylindrical insulating member 130 from the radially outer side at the projections 215c of the outer tubular portion 215 and to the protruding portions 151b of the output side terminal portion 151 from the radially inner side at the conductive portion 216a. For this reason, when the sensor cap 200 is attached to or detached from the gas sensor 100 by moving the cap terminal 210 in the direction along the axis CX (AX) (vertically in FIG. 1), the sensor cap 200 can be easily attached or detached, and the attaching and detaching feature is excellent.

Furthermore, in the gas sensor unit 300 in accordance with the first embodiment, as described above, the communicating hole 223d is provided in the lead enclosing portion 223 of the sensor cap 200, and the communicating hole 223d is closed by the filter member 240 which is gas permeable and water repellent. For this reason, as indicated by the broken-line arrows in FIG. 1, through this filter member 240, passage of gas can be carried out between the external space SPO and the internal space SPI formed by the gas sensor 100 and the sensor cap 200. Accordingly, rapid ventilation of the internal space SPI can be effected. In addition, it is also possible to supply outside air (reference gas) to the inside of the gas detecting element 120 of the gas sensor 100 via the interior of the enclosing member 220 defining the vent passage P and the interior of the sensor terminal 150.

Moreover, filter member 240 has an inserting hole 241 in its center, and the lead wire 230 is watertightly inserted therein. For this reason, through the communicating hole 223d the lead wire 230 can be led to the outside wile entry of water into the internal space SPI is prevented.

(First Modification)

Figure 6A:
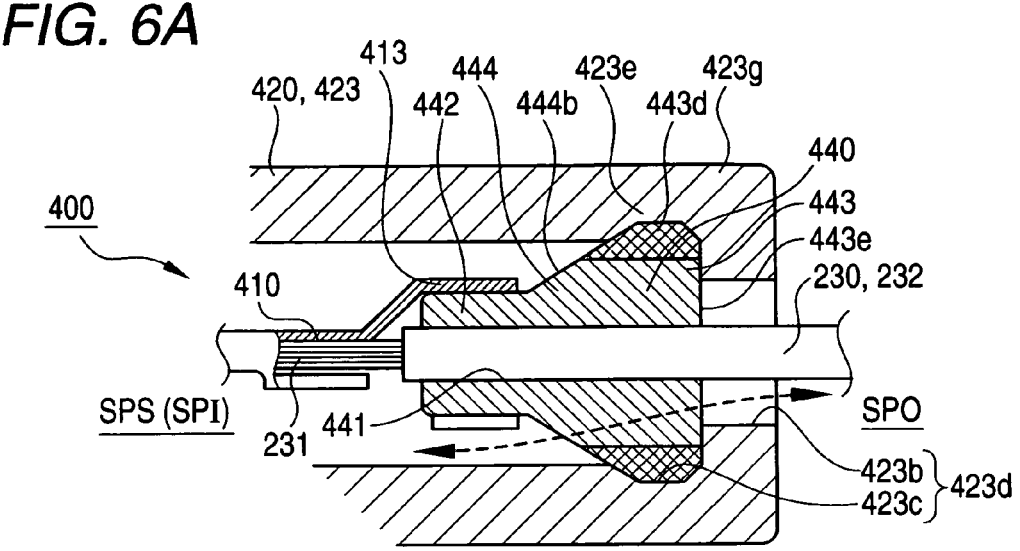

Next, referring to FIG. 6A, a description will be given of a sensor cap 400 in accordance with a first modification of the above-described first embodiment. The sensor cap 400 of this first medication differs from the sensor cap 200 of the above-described first embodiment in the form of a lead enclosing portion 423 in an enclosing member 420, particularly the shape of a filter member 440. Accordingly, a description of similar portions will be omitted or simplified, and a description will be given focusing on different portions.

In the sensor cap 200 in accordance with the above-described first embodiment, a filter member 240 is used which has a main body 243 of relatively large diameter and a crimping portion 242 of smaller diameter than the main body 243, as well as a step surface 243f formed therebetween in a stepped shape and perpendicularly to the axis LX (see FIG. 3).

In contrast, the sensor cap 400 of the first modification similarly has a main body 443 of relatively large diameter and a crimping portion 442 of smaller diameter than the main body 443. However, a tapered portion 444 having a step surface 444b where the diameter becomes gradually smaller toward the crimping portion 442 is provided therebetween, Accordingly, if the crimping portion 442 is crimped by a filter crimping portion 413 of a cap terminal 410, in the same way as in the first embodiment, the filter member 440 and the cap terminal 410 become integrated, and the lead wire 230 inserted in an inserting hole 441 can be watertightly integrated with the filter member 440. It should be noted, however, that there are cases where the gas permeability in the crimping portion 442 declines or is lost.

However, the filter member 440 of the first modification has a tapered portion 444 and passage of gas between the inner and outer sides is possible through the step surface 444b (outer peripheral surface of the tapered portion 444) which bridges the difference in diameter between the main body 443 and the crimping portion 442. For this reason, as indicated by the broken-line arrows in FIG. 6A, gas permeability is provided between the external space SPO and the cap terminal accommodating space SPS, specifically between a gas permeable surface 443e of the main body 443 facing the external space SPO and the step surface 444b of the tapered portion 444 facing the cap terminal accommodating space SPS. Thus, rapid ventilation of the internal space SPI of the sensor cap 400 of the first modification can be effected, and it is possible to supply outside air (reference gas) to the inside of the gas detecting element 120 of the gas sensor 100.

It should be noted that the outer peripheral portion of the main body 443 is formed as an outer peripheral close contact portion 443d in the same way as in the above-described first embodiment. Accordingly, the outer peripheral portion of the main body 443 can be brought into close contact with the filter holding portion 423e of the lead enclosing portion 423 without leaving a gap. Hence, the filter member 440 can be watertightly held more reliably.

In addition, in the same way as in the above-described first embodiment, the lead enclosing portion 423 has at a position adjacent to the filter holding portion 423e a holding portion 423g which juts out inwardly of that portion and which defines a small-diameter vent hole 423b having a small diameter. By virtue of the presence of this holding portion 423g, the filter member 440 is held in place, that is, the filter member 440 is prevented from coming out of communicating hole 423d (small-diameter vent hole 423b) to the outside (to the right side in the drawing).

(Second Modification)

Figure 6B:
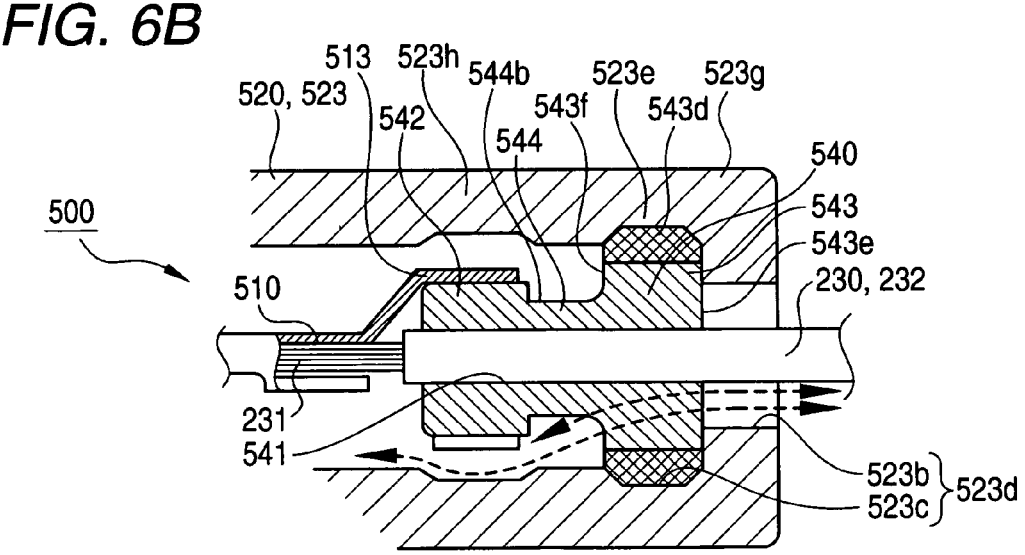

Next, referring to FIG. 6B, a description will be given of a sensor cap 500 in accordance with a second modification of the above-described first embodiment. The sensor cap 500 of this second medication also differs from the sensor cap 200 in accordance with the above-described first embodiment in the form of a lead enclosing portion 523 in an enclosing member 520, particularly the shape of a filter member 540. Accordingly, a description of similar portions will be omitted or simplified, and a description will be given focusing on different portions.

In the same way as in the first embodiment, the sensor cap 400 of this second modification has a main body 543 of a relatively large diameter and a crimping portion 542 of smaller diameter than the main body 543. However, a small-diameter intermediate portion 544 having a smaller diameter than these portions is provided therebetween.

Accordingly, if the crimping portion 542 is crimped by a filter crimping portion 513 of a cap terminal 510, the filter member 540 and the cap terminal 510 become integrated, and the lead wire 230 inserted in an inserting hole 541 can be watertightly integrated with the filter member 540. It should be noted, however, that there are cases where the gas permeability in the crimping portion 542 declines or is lost.

However, the filter member 540 of the second modification has a small-diameter intermediate portion 544, and passage of gas between the inner and outer sides is possible through a step surface 543f which bridges the difference in diameter between the main body 543 and the small-diameter intermediate portion 544. For this reason, as indicated by the broken-line arrows in FIG. 6B, gas permeability is provided between the external space SPO and the cap terminal accommodating space SPS, specifically between a gas permeable surface 543e of the main body 543 facing the external space SPO and the step surface 543f facing the cap terminal accommodating space SPS.

It should be noted that, in the second modification, the outer peripheral surface of the small-diameter intermediate portion 544 is formed as a gas permeable outer peripheral surface 544b which is not provided with smoothing treatment and is gas permeable. For this reason, the passage of gas with respect to the cap terminal accommodating space SPS is also possible through the gas permeable outer peripheral surface 544b.

Thus, also with the sensor cap 500 of the second modification, rapid ventilation of the internal space SPI and the supply of reference gas to the interior of the gas detecting element 120 are made possible.

It should be noted that the outer peripheral portion of the main body 543 is formed as an outer peripheral close contact portion 543d in the same way as in the above-described first embodiment. Accordingly, the outer peripheral portion of the main body 543 can be brought into close contact with the filter holding portion 523e of the lead enclosing portion 523 without leaving a gap. Hence, the filter member 540 can be watertightly held more reliably.

In addition, in the same way as in the above-described first embodiment, the lead enclosing portion 523 has at a position adjacent to the filter holding portion 523e a holding portion 523g which juts out inwardly of that portion and which defines a small-diameter vent hole 523b having a small diameter. By virtue of the presence of this holding portion 523g, the filter member 540 is held in place, that is, the filter member 540 is prevented from coming out of communicating hole 523d (small-diameter vent hole 523b) to the outside (to the right side in the drawing). In addition, a thin-walled portion 523h is formed at a position on this lead enclosing portion 523 corresponding to the crimping portion 542, thereby facilitating the passage of gas.

(Third Modification)

Figure 6C:
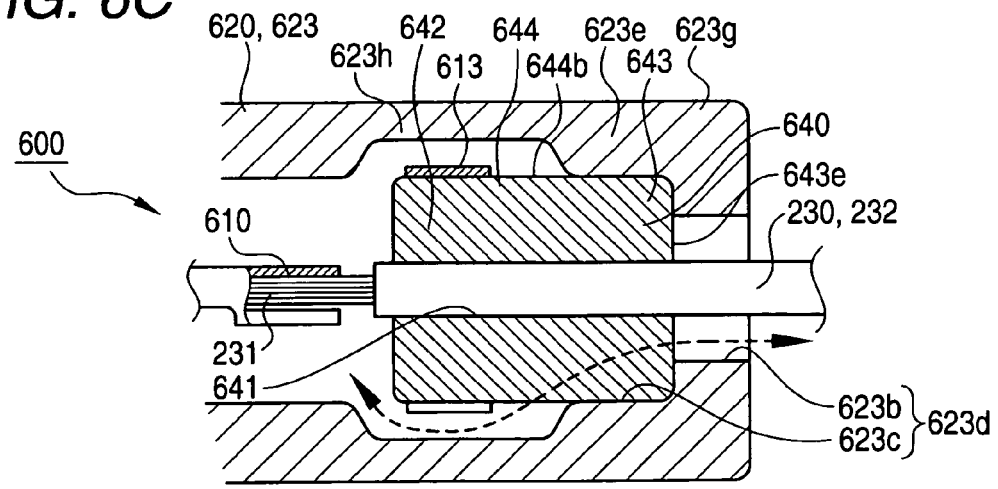

Next, referring to FIG. 6C, a description will be given of a sensor cap 600 in accordance with a third modification of the above-described first embodiment. The sensor cap 600 of this third medication also differs from the sensor cap 200 in accordance with the above-described first embodiment in the form of a lead enclosing portion 623, particularly the shape of a filter member 640. Accordingly, a description of similar portions will be omitted or simplified, and a description will be given focusing on different portions.

The sensor cap 600 of this third modification has a filter member 640 in a lead enclosing portion 623 in an enclosing member 620 in the same way as in the first embodiment. However, the filter member 640 has a substantially hollow cylindrical shape, and the diameters of its main body 643 and crimping portion 642 are substantially identical in diameter at least before crimping. Further, an intermediate vent portion 644 of the same diameter is provided therebetween. In addition, although the filter crimping portion 213 is integrally provided on the cap terminal 210 in the first embodiment and the like, in this third modification, the crimping portion 642 is crimped by a C-shaped crimping member 613 separately from a cap terminal 610. As a result, the lead wire 230 inserted in an inserting hole 641 can be watertightly integrated with the filter member 640. It should be noted, however, that there are cases where the gas permeability in the crimping portion 642 declines or is lost.

However, the filter member 640 of the third modification has an intermediate vent portion 644 between the main body 643 and the crimping portion 642, and since this outer peripheral surface is a gas permeable outer peripheral surface 644b which is gas permeable, the passage of gas between the inner and outer sides is possible through this surface. For this reason, as indicated by the broken-line arrows in FIG. 6C, gas permeability is provided between the external space SPO and the cap terminal accommodating space SPS, specifically between a gas permeable surface 643e of the main body 643 facing the external space SPO and the gas permeable outer peripheral surface 644b of the intermediate vent portion 644 facing the cap terminal accommodating space SPS.

It should be noted that, in the third modification, the gas permeable outer peripheral surface 644b of the intermediate vent portion 644 is not provided with smoothing treatment.

Thus, rapid ventilation of the internal space SPI with the sensor cap 600 of the third modification, and supply of reference gas to the interior of the gas detecting element 120 are made possible.

It should be noted that the outer peripheral portion of the main body 643 might be provided with smoothing treatment, although not shown, in the same way as in the above-described first embodiment. If smoothing treatment is provided, it is possible to further improve close contact with a filter holding portion 623e of the lead enclosing portion 623 and improve watertightness.

In addition, in the same way as in the above-described first embodiment, the lead enclosing portion 623 has at a position adjacent to the filter holding portion 623e a holding portion 623g which juts out inwardly of that portion and which defines a small-diameter vent hole 623b having a small diameter. The filter member 640 is held in place, that is, the filter member 640 is prevented from coming out of communicating hole 623d (small-diameter vent hole 623b) to the outside (to the right side in the drawing). In addition, a thin-walled portion 623h is formed at a position on this lead enclosing portion 623 corresponding to the crimping portion 642 and the intermediate vent portion 644, thereby facilitating the passage of gas.

(Fourth Modification)

Figure 7:
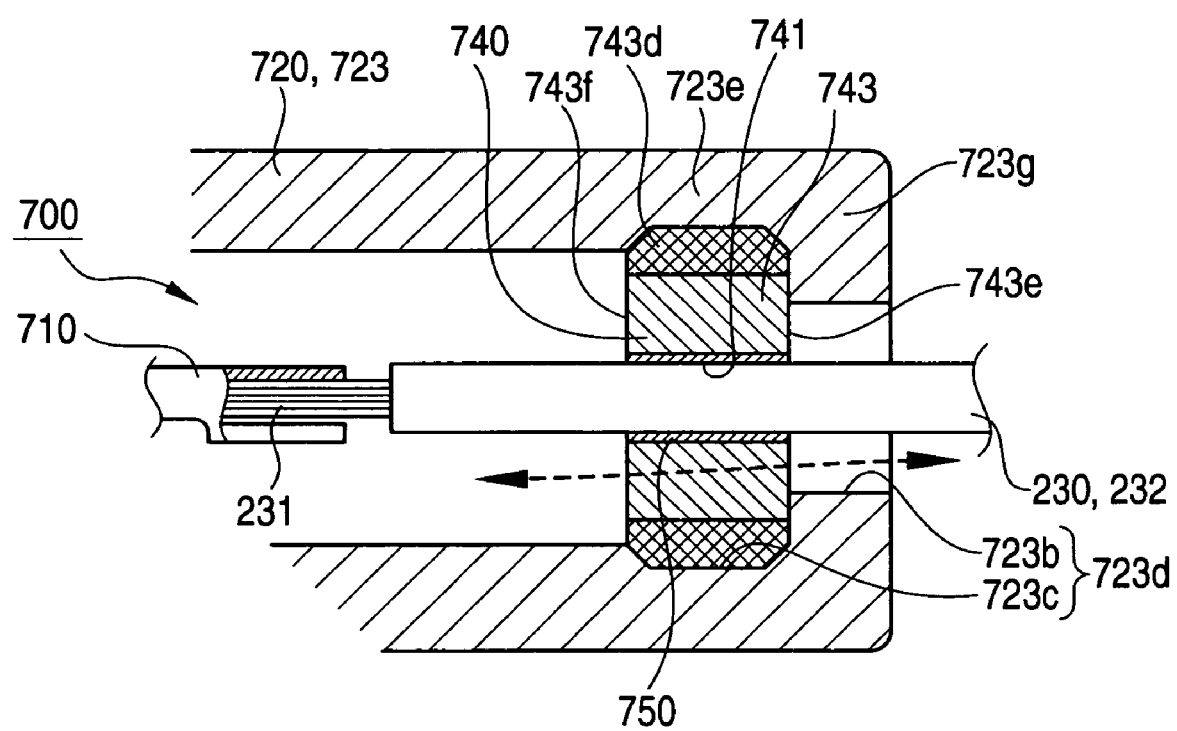
FIG. 7 is a partial cross-sectional view illustrating characteristic features of the sensor cap in accordance with a fourth modification.

Next, referring to FIG. 7, a description will be given of a sensor cap 700 in accordance with a fourth modification of the above-described first embodiment. In the above-described first embodiment and first to third modifications, the lead wire 230 is watertightly integrated with the filter member 240 and the like by crimping the filter member 240 and the like. In contrast, the sensor cap 700 in accordance with the fourth modification differs in that the lead wire is fixed to the filter member without resorting to crimping of the filter member, and other aspects are the same. Accordingly, a description of similar portions will be omitted or simplified, and a description will be given focusing on different portions.

In the above-described first embodiment, the filter member 240 includes the main body 243 and the crimping portion 242. In contrast, in the sensor cap 700 of the fourth modification, a filter member 740 consists of only a main body 743 corresponding to the main body 243 in the first embodiment. In addition, the filter member 740 of this fourth modification has an inserting hole 741 whose diameter is larger than the outside diameter of the lead wire 230 (first covering 232), and this lead wire 230 is loosely inserted therein. The lead wire 230 (first covering 232) is watertightly secured using a bonding seal material 750 formed from a resin filled in the inserting hole 741.

By virtue of this filter member 740, gas permeability is provided between the external space SPO and the cap terminal accommodating space SPS, specifically between an outer gas permeable surface 743e of the main body 743 facing the external space SPO and an inner gas permeable surface 743f facing the cap terminal accommodating space SPS. Thus, rapid ventilation of the internal space SPI can be effected with the sensor cap 700 of the fourth modification, and it is possible to supply outside air (reference gas) to the inside of the gas detecting element 120 of the gas sensor 100.

It should be noted that the outer peripheral portion of the filter member 740 (main body 743) is formed as an outer peripheral close contact portion 743d in the same way as in the above-described first embodiment. Accordingly, the outer peripheral portion of the filter member 740 can be brought into close contact with a filter holding portion 723e of the lead enclosing portion 723 without leaving a gap. Hence, the filter member 740 can be watertightly held more reliably.

In addition, in the same way as in the above-described first embodiment and first to third modifications, at a position on the lead enclosing portion 723 which is adjacent to the filter holding portion 723e, a holding portion 723g is formed which juts out inwardly of that portion and which defines a small-diameter vent hole 723b having a small diameter. The filter member 740 is thereby held in place, that is, the filter member 740 is prevented from coming out of communicating hole 723d (small-diameter vent hole 723b) to the outside (to the right side in the drawing).

Second Embodiment

Figure 8:
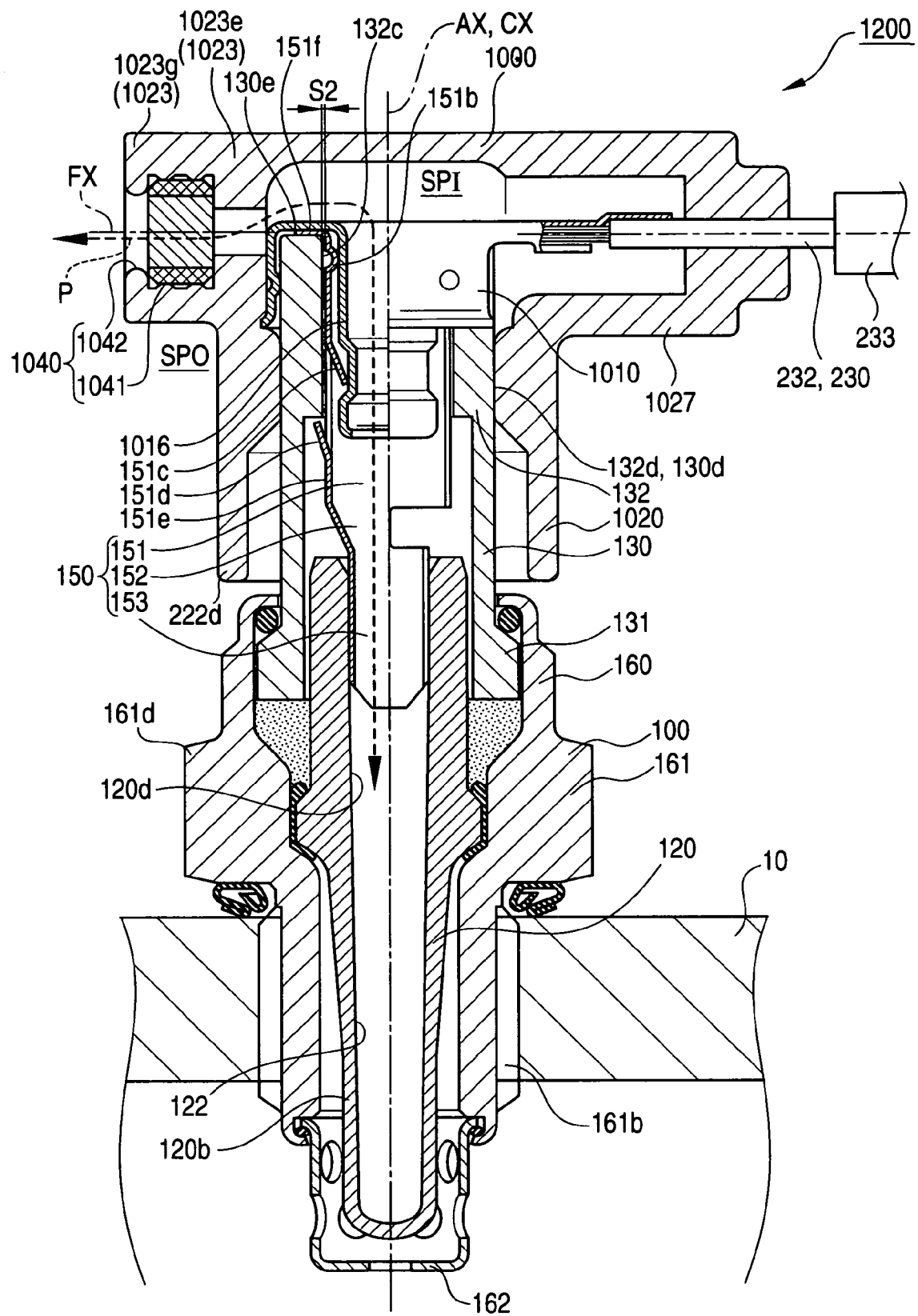
FIG. 8 is an explanatory diagram illustrating a gas sensor unit 1200 in accordance with a second embodiment and the manner in which this gas sensor unit is put to use.

Next, referring to FIGS. 8 to 10, a description will be given of a gas sensor unit 1200 and a sensor cap 1000 in accordance with a second embodiment. As compared with the gas sensor unit 300 of the first embodiment, the gas sensor unit of this second embodiment differs only in the sensor cap, and the gas sensor is identical. Specifically, as shown in FIG. 8, the gas sensor 100 identical to that of the first embodiment and a sensor cap 1000 different from that of the first embodiment is provided.

As compared with the sensor cap 200 of the first embodiment, the sensor cap 1000 of the second embodiment differs in the form of the enclosing member and in the form of the filter member and its layout position, and other portions are substantially similar. Accordingly, a description will be given below of the sensor cap 1000 of the second embodiment, focusing on portions different from those of the sensor cap 200 of the first embodiment.

In the sensor cap 200 of the first embodiment, as shown in FIG. 3, by using the filter member 240 provided with the inserting hole 241, the lead wire 230 (first covering 232) is inserted in the inserting hole 241, and the filter member 240 together with the lead wire 230 is provided in the lead enclosing portion 223.

Figure 9:
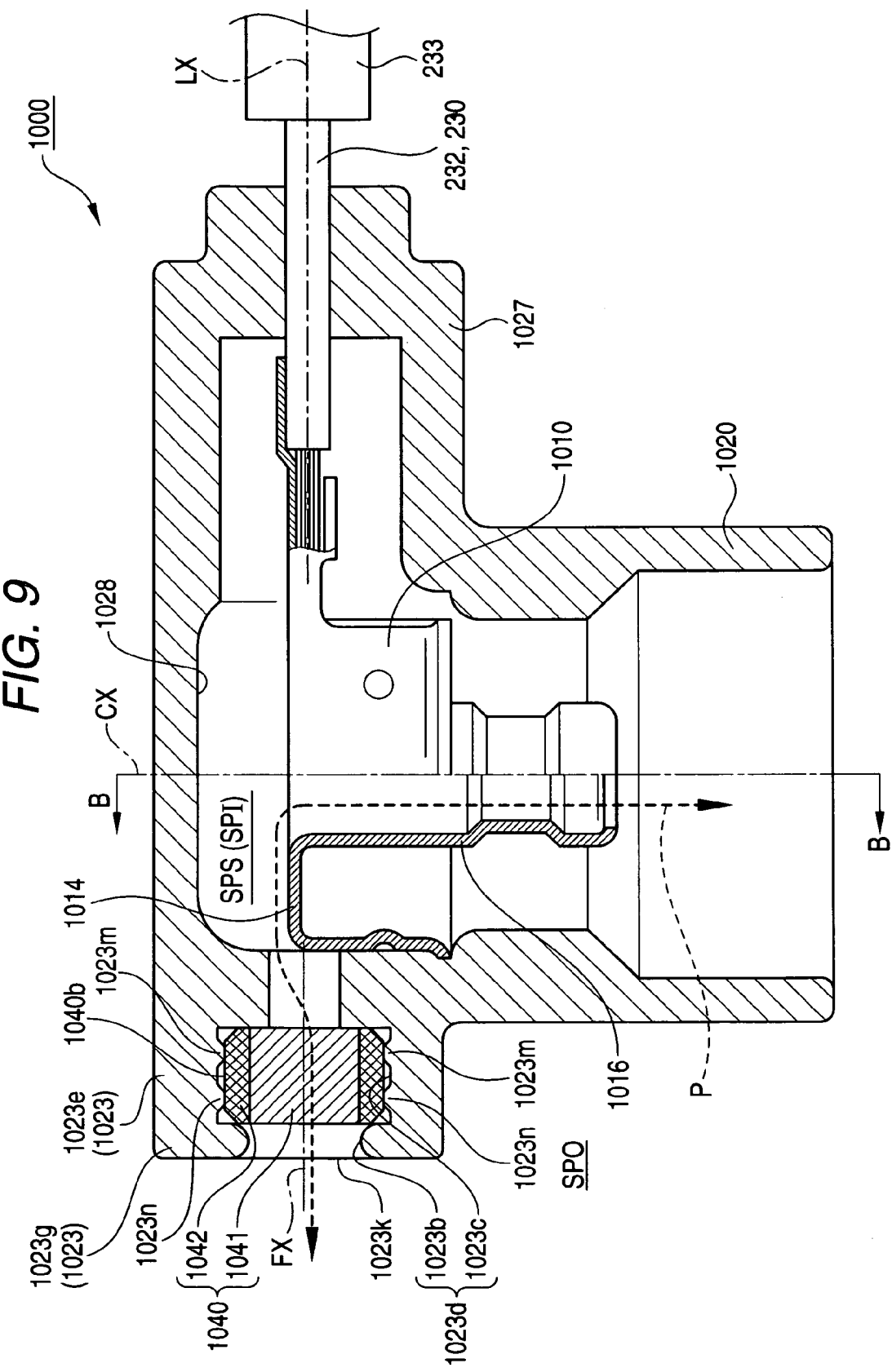
FIG. 9 is a partial cross-sectional view of a sensor cap 1000 in accordance with the second embodiment.

In contrast, in the sensor cap 1000 of the second embodiment, as shown in FIG. 9, a filter member 1040 not having an inserting hole is used, and this filter member 1040 is provided in a filter enclosing portion 1023 provided separately from a lead enclosing portion 1027.

Specifically, the filter member 1040 is a filter member which consists of a cylindrical center portion 1041 and an outer peripheral close contact portion 1042 which annularly surrounds this center portion 1041. In addition, an enclosing member 1020 has a communicating hole 1023d (small-diameter vent hole 1023b and a filter holding hole 1023c) provided on the opposite side to the lead enclosing portion 1027 as viewed from the axis CX unlike the first embodiment. As a result, the filter member 1040 is provided in the filter holding hole 1023c separately from the lead wire 230.

Further, in the second embodiment annular protruding portions 1023m and 1023n protruding inwardly (toward the side of an axis FX of the filter member 1040) are provided in a filter holding portion 1023e defining the filter holding hole 1023c These annular protruding portions 1023m and 1023n are held in close contact with an outer peripheral surface 1040b of the filter member 1040 to hold the filter member 1040. Namely, unlike the first embodiment, the inner wall surface of the filter member 1023e is not brought into close contact with the overall outer peripheral surface 1040b of the filter member 1040 (outer peripheral close contact portion 1042), but the annular protruding portions 1023m and 1023n are brought into close contact with the outer peripheral surface 1040b of the filter member 1040, and are thereby brought into close contact only with portions of the outer peripheral surface 1040b. As a result, the closely contacting force of the inner wall surface of the filter holding portion 1023e with respect to the outer peripheral surface 1040b of the filter member 1040 is enhanced, thereby making it possible to increase the watertightness between the filter member 1040 and the filter holding portion 1023e.

Moreover, the filter enclosing portion 1023 defining the communicating hole 1023d has at a position (adjacent on the left side in FIG. 9) adjacent to the filter holding portion 1023e a holding portion 1023g whose diameter is smaller than that of this filter holding portion 1023e. This holding portion 1023g has a form in which it juts out inwardly (toward the axis FX side) of the filter holding portion 1023e. By virtue of the holding portion 1023g which juts out toward the axis FX, the filter member 1040 is held in place, that is, the filter member 1040 is prevented from coming out of the communicating hole 1023d (small-diameter vent hole 1023b) to the outside (to the left side in FIG. 9).

It should be noted that as the filter member 1040 is pressed in toward the inner side (in the rightward direction in FIG. 9) through an opening 1023k of the filter enclosing portion 1023 while resiliently deforming the holding portion 1023g in such manner as to enlarge its inside diameter, the filter member 1040 can be provided inside the filter holding hole 1023c.

Figure 10:
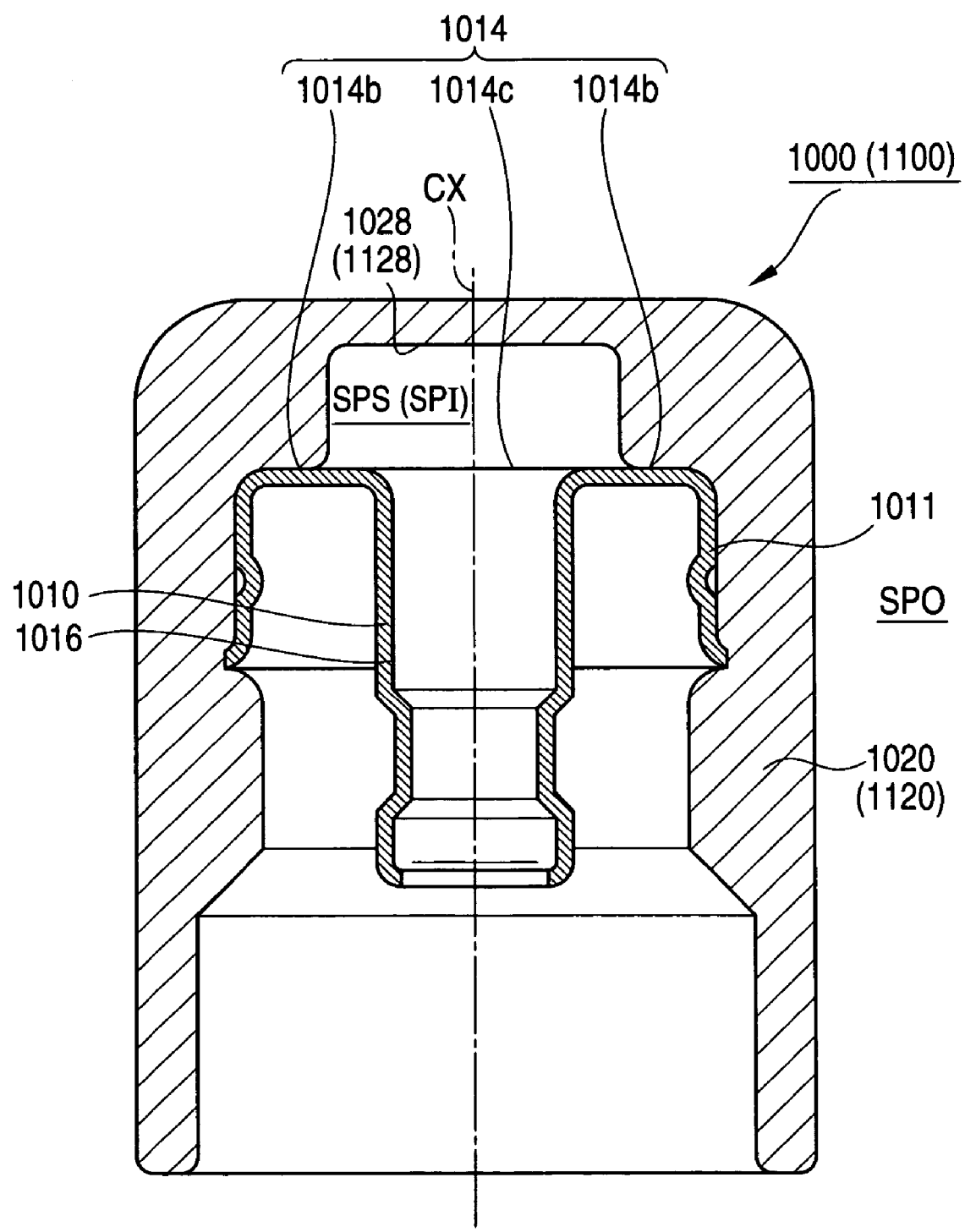
FIG. 10 is a partial cross-sectional view taken along line B-B in the direction of the arrows in FIG. 9, and is a partial cross-sectional view taken along line D-D in the direction of arrows in FIG. 11.

In addition, as shown in FIG. 10, in a sensor connecting portion 1011 (corresponding to the tubular portion) of the cap terminal 1010, an annular end portion 1014 (corresponding to the end portion) provided on the first-moving-direction side (upper side in FIG. 10) has a contact portion 1014b abutting an inner surface 1028 of the enclosing member 1020. Namely, the cap terminal 1010 abuts the inner surface 1028 of the enclosing member 1020 in the first moving direction (upwardly in FIG. 10). For this reason, in the same way as in the first embodiment, when the sensor cap 1000 is joined to the gas sensor 100, the cap terminal 1010 can be connected to the sensor terminal 150 in a state in which movement of the cap terminal 1010 in the first moving direction is restricted.

Accordingly, in this second embodiment, when the sensor cap 1000 and the gas sensor 100 are assembled, because the annular end portion 1014 of the cap terminal 1010 abuts the stopper portion 151f of the gas sensor 100, there is no possibility of the cap terminal 1010 becoming positionally offset in the first moving direction (in the upward direction along the axis CX in FIG. 10). For this reason, if the sensor cap 1000 and the gas sensor 100 are joined by abutting the annular end portion 1014 of the cap terminal 1010 against the stopper portion 151f of the gas sensor 100, it is possible to form the gas sensor unit 1200 in which the cap terminal 1010 and the sensor terminal 150 are connected appropriately in place, as shown in FIG. 8.

Moreover, as shown in FIG. 10, the annular end portion 1014 of the cap terminal 1010 has a non-contact portion 1014c which is spaced apart from the inner surface 1028 of the enclosing member 1020. Namely, the cap terminal accommodating space SPS (internal space SPI) is enlarged between the annular end portion 1014 of the cap terminal 1010 and the inner surface 1028 of the enclosing member 1020, thereby allowing a portion of the vent passage P (indicated by the broken-line arrows in FIG. 9) for the reference gas introduced from the outside to be formed between the annular end portion 1014 of the cap terminal 1010 and the inner surface 1028 of the enclosing member 1020. For this reason, outside air (reference gas) introduced from the external space SPO through the communicating hole 1023d can be introduced into the tube of an inner tubular portion 1016 of the cap terminal 1010 through the space between the non-contact portion 1014c of the cap terminal 1010 and the inner surface 1028 of the enclosing member 1020. Accordingly, it becomes possible to introduce outside air (reference gas) to the inside of the gas detecting element 120 of the gas sensor 100, as indicated by the broken-line arrows in FIG. 8.

(Fifth Modification)

Next, referring to FIGS. 10 to 12, a description will be given of a sensor cap 1100 in accordance with a fifth modification of the above-described second embodiment. As compared with the sensor cap 1000 of the second embodiment, the sensor cap 1100 of this fifth modification differs in the form of the filter enclosing portion (more particular, the communicating hole), and other aspects are substantially the same. Accordingly, a description of portions similar to those of the second embodiment will be omitted or simplified, and a description will be given focusing on different portions.

As shown in FIG. 9, in the sensor cap 1000 of the second embodiment, the communicating hole 1023d is formed as the through hole concentric with the axis FX of the filter member 1040. For this reason, the presence of filter member 1040 can be visually confirmed through the opening 1023k of the communicating hole 1023d. However, in a case where the gas sensor unit in which this sensor cap 1000 is fitted to the gas sensor 100 is installed in a vehicle, for example, and the vehicle is washed with a high-pressure cleaning machine, there is a possibility of high-speed water entering the opening 1023k and directly reaching the filter member 1040. In this case, there is a possibility that water pressure exceeding the water pressure resistance of the filter member 1040 is applied to the filter member 1040, causing water droplets to undesirably permeate the filter member 1040.

Figure 11:
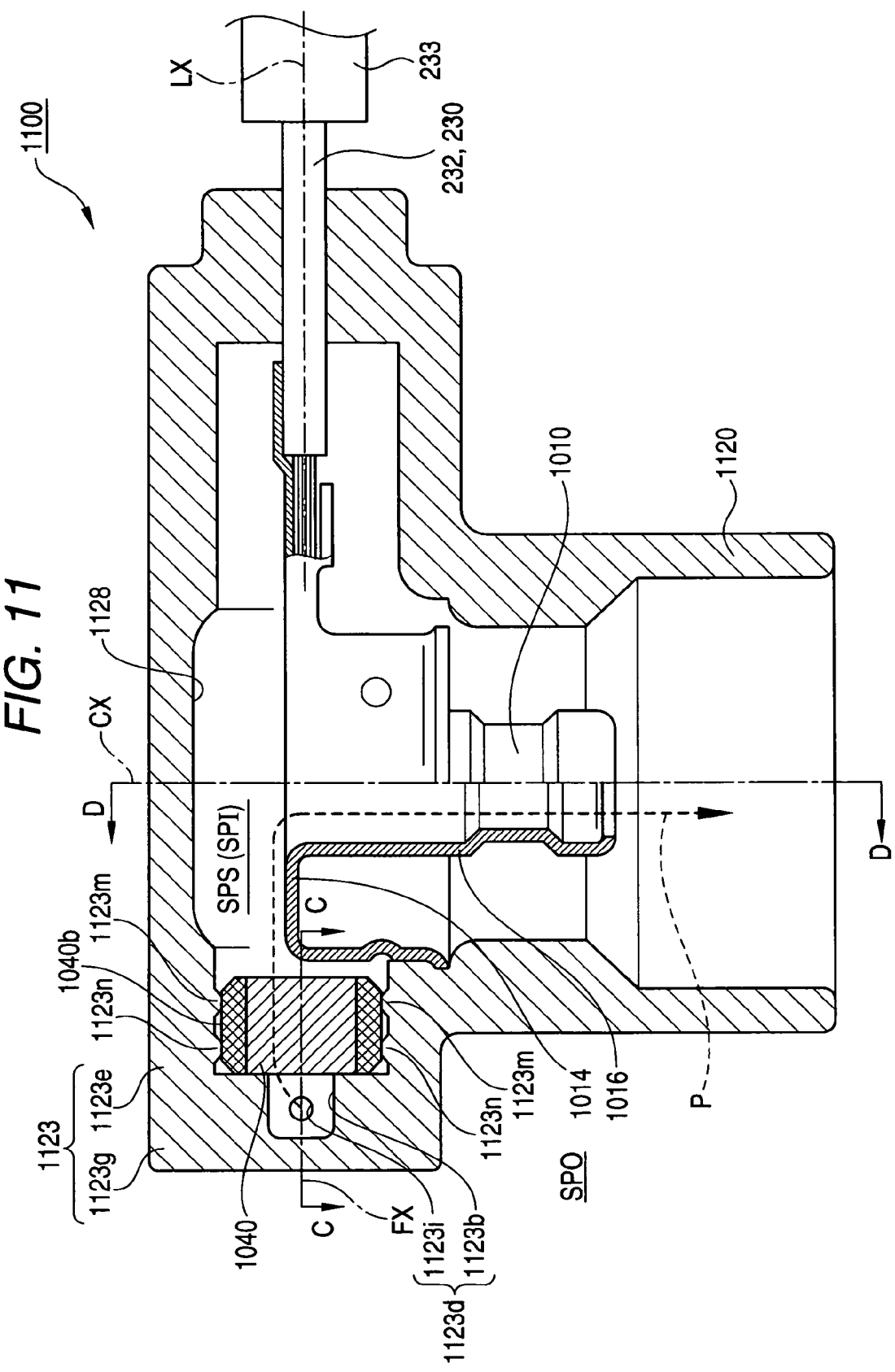
FIG. 11 a partial cross-sectional view of a sensor cap 1100 in accordance with a fifth modification.

In contrast, with the sensor cap 1100 of the fifth modification, as shown in FIG. 11, in a filter enclosing portion 1123, a holding portion 1123g defining a small-diameter vent hole 1123b is formed so as to have the shape of a bottomed tube and which is not open in an outward direction along the axis FX (in the leftward direction in FIG. 11). Further, a through hole 1123h (see FIG. 12) and a through hole 1123i which communicate with the small-diameter vent hole 1123b are provided so as to extend through the holding portion 1123g in a direction perpendicular to the axis FX (in a direction perpendicular to the plane of the drawing in FIG. 11). As a result, as indicated by the broken-line arrows in FIG. 11, the passage of gas can be provided appropriately between the external space SPO and the cap terminal accommodating space SPS (internal space SPI) through the through holes 1123h and 1123i and the small-diameter vent hole 1123b.

However, with the sensor cap 1100 of the fifth modification, as shown by the arrows KS1 and KS2 of the two-dot chain lines, the through holes 1123h and 1123i are provided at positions where the filter member 1040 cannot be visually confirmed through openings 1123kh and 1123ki of the through holes 1123h and 1123i. In other words, the filter member 1040 is provided at a position where it cannot be visually confirmed through both the openings 1123kh and 1123ki of the through holes 1123h and 1123i.

For this reason, even in a case where water enters at high speed from the outside through the openings 1123kh and 1123ki, this high-speed water does not directly reach the filter member 1040. Namely, the water which enters at high speed from the outside through the openings 1123kh and 1123ki collides against inner wall surfaces of the holding portion 1123g defining the through holes 1123h and 1123i and the small-diameter vent hole 1123b before reaching the filter member 1040, making it possible to attenuate its force (speed). Accordingly, even in cases where water enters at high speed from the outside through the openings 1123*kh* and 1123*ki*, it is possible to keep the water from infiltrating the filter member 1040.

Further, in the sensor cap 1100 of the fifth modification, two openings (openings 1123*kh* and 1123*ki*) are provided for a communicating hole 1123*d* which is open to the outside. As a result, even if water continues to enter at high speed from one opening (e.g., opening 1123*kh*), the water can be discharged to the outside through the other opening (e.g., opening 1123*ki*).

Figure 12:
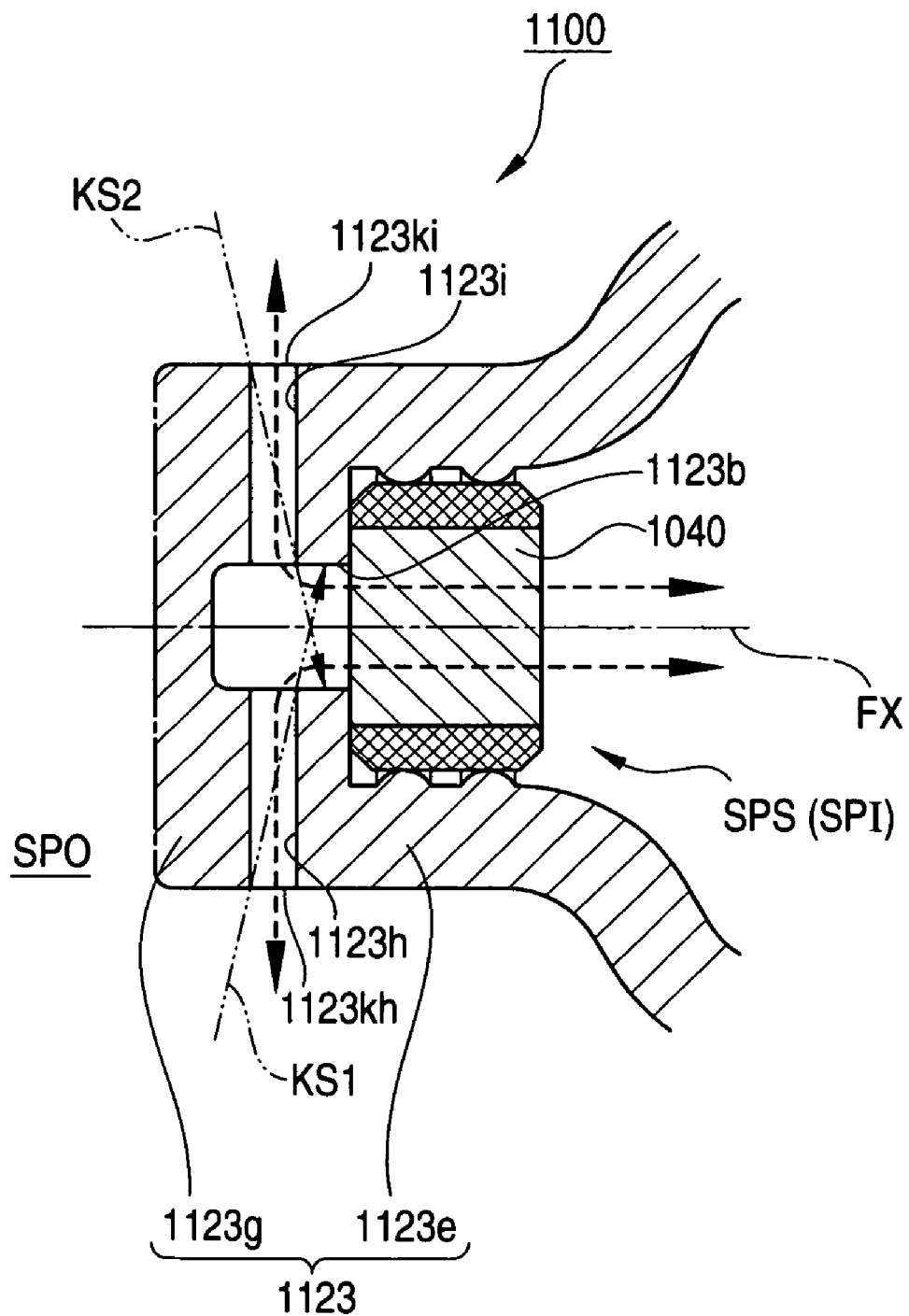
FIG. 12 is a cross-sectional view taken along line C-C in the direction of arrows in FIG. 11.

In particular, in the fifth modification, as shown in FIG. 12, the through holes 1123*h* and 1123*i* are provided at mutually opposing positions with the small-diameter vent hole 1123*b* provided therebetween. For this reason, water which enters at high speed from, one opening (e.g., opening 1123*kh*) is smoothly discharged to the outside through the other opening (e.g., opening 1123*ki*). Accordingly, there is no possibility of high water pressure being applied to the filter member 1040, so that there is no possibility of water droplets permeating the filter member 1040.

In addition, as shown in FIG. 11, in the fifth modification as well, in the same manner as in the second embodiment, annular protruding portions 1123*m* and 1123*n* protruding inwardly (toward the axis FX side) are provided in a filter holding portion 1123*e*. These protruding portions 1123*m* and 1123*n* are held in close contact with the outer peripheral surface 1040*b* of the filter member 1040 to hold the filter member 1040. As a result, the closely contacting force of the inner wall surface of the filter holding portion 1123*e* with respect to the outer peripheral surface 1040*b* of the filter member 1040 is enhanced, thereby making it possible to increase the watertightness between the filter member 1040 and the filter holding portion 1123*e*.

In addition, as shown in FIG. 10, according to the fifth modification as well, in the same way as in the second embodiment, in the sensor connecting portion 1011 (corresponding to the tubular portion) of the cap terminal 1010, the annular end portion 1014 (corresponding to the end portion) provided on the first-moving-direction side (upper side in FIG. 10) has the contact portion 1014*b* abutting an inner surface 1128 of an enclosing member 1120. Namely, the cap terminal 1010 abuts the inner surface 1128 of the enclosing member 1120 in the first moving direction (upwardly in FIG. 10). For this reason, in the same way as in the first embodiment, when the sensor cap 1100 is connected to the gas sensor 100, the cap terminal 1010 can be connected to the sensor terminal 150 in a state in which movement of the cap terminal 1010 in the first moving direction is restricted.

Accordingly, in this fifth modification as well, when the sensor cap 1100 and the gas sensor 100 are assembled, even if the annular end portion 1114 of the cap terminal 1010 is positioned to abut the stopper portion 151*f* of the gas sensor 100 there is no possibility of the cap terminal 1010 becoming positionally offset in the first moving direction. For this reason, if the sensor cap 1100 and the gas sensor 100 are joined by abutting the annular end portion 1014 of the cap terminal 1010 against the stopper portion 151*f* of the gas sensor 100, the cap terminal 1010 and the sensor terminal 150 can be connected appropriately in place.

Furthermore, in the same way as in the second embodiment, as shown in FIG. 10, the annular end portion 1014 of the cap terminal 1010 has a non-contact portion 1014*c* which is spaced apart from the inner surface 1128 of the enclosing member 1120. Namely, the cap terminal accommodating space SPS (internal space SPI) is enlarged between the annular end portion 1014 of the cap terminal 1010 and the inner surface 1128 of the enclosing member 1120, thereby allowing a portion of the vent passage P (indicated by the broken-line arrows in FIG. 11) for the reference gas introduced from the outside to be formed between the annular end portion 1014 of the cap terminal 1010 and the inner surface 1128 of the enclosing member 1120. For this reason, the outside air (reference gas) introduced from the external space SPO through the communicating hole 1123*d* can be introduced into the tube of the inner tubular portion 1016 of the cap terminal 1010 through the space between the non-contact portion 1014*c* of the cap terminal 1010 and the inner surface 1128 of the enclosing member 1120. Accordingly, even if the sensor cap 1100 of the fifth modification is used, in the same way as in the second embodiment, it becomes possible to introduce outside air (reference gas) to the inside of the gas detecting element 120 of the gas sensor 100, as indicated by the broken-line arrows in FIG. 11.

Although a description has been given above of the first and second embodiments and first to fifth modifications, the invention is not limited to the above-described embodiments and the like, and it is to be understood that various modifications to the invention can be made within a scope that does not depart from the gist of the invention.

For example, in the above-described first embodiment, a case is shown in which the filter member 240 and the like are provided with the inserting hole 241, and the lead wire 230 is passed through this inserting hole 241. However, an arrangement may be provided such that the lead wire is led out separately from another portion of the enclosing member, and the filter member is used to effect the passage of gas (ventilation).

In addition, in the first embodiment and the first and second modifications, the crimping portion 242 of the filter member 240 and the like are crimped by the filter crimping portion 213 which is a portion of the cap terminal 210. However, it is not necessary to use a portion of the cap terminal 210 and the like in order to crimp the crimping portion 242 and the like, and the crimping portion may be crimped using a crimping member prepared separately from the cap terminal.

Further, in the first embodiment and the first to third modifications, the crimping portion 242 is provided on the inner side of the main body 243 of the filter member 240 (on the cap terminal accommodating space SPS side, the side of the sensor connecting portion of the cap terminal, or the left side in FIG. 3). However, the crimping portion may be provided on the outer side of the main body (on the external space side, the small-diameter vent hole side, or the right side in FIG. 3), and this portion may be crimped by a crimping member. Furthermore, this crimping portion may be provided inside the small-diameter vent hole.

In addition, in the embodiments and the like, a form is shown in which the filter member 240 and the like are not provided in the small-diameter vent hole 223*b*.

However, it is also possible to use a filter member having a three-step form including small, large and small diameter portions, in which an outer protruding portion 245 protruding from the, holding portion 223*g* is further provided in the small-diameter vent hole 223*b*, as shown by the broken lines in FIG. 3. If a cavity due to the small-diameter vent hole 223*b* is eliminated by thus providing the outer protruding portion 245, in a case where this gas sensor unit is used in a form in which, for example, the axis LX agrees with a vertical line and the sensor connecting portion 211 is provided below the filter member 240 in the sensor cap 200, it is possible to prevent a malfunction in which water otherwise accumulates in the small-diameter vent hole 223b, rendering the passage of gas through the filter member difficult.

It should be noted that if the crimping portion is provided in the small-diameter vent hole as described above, it is possible to eliminate the cavity due to the small-diameter vent hole 223b. Accordingly, it suffices if the cavity due to the small-diameter vent hole 223b can be eliminated by the filter member.

This application is based on Japanese Patent Application JP 2004-330347, filed Nov. 15, 2004, the entire content of which is hereby incorporated by reference, the same as if set forth at length.

What is claimed is:

1. A gas sensor unit comprising:
a gas sensor including a gas detecting element, an electrode provided on the gas detecting element and a sensor terminal connecting to the electrode so as to transmit an output signal from the gas detecting element; and
a sensor cap for transmitting the output signal to an external device, the sensor cap including a cap terminal electrically connecting to the sensor terminal and an enclosing member bonding to the gas sensor so as to form an internal space in cooperation with the gas sensor, said cap terminal resiliently connecting to the sensor terminal so that the gas sensor and the gas sensor cap are detachable from one another,
wherein the enclosing member includes a communicating hole through which the internal space is in communication with space outside the gas sensor unit, and the communicating hole is gas-permeably and watertightly closed by a filter member.

2. The gas sensor unit as claimed in claim 1, wherein at least one of the enclosing member and the filter member comprises a resilient material, and an inner wall surface of the communicating hole and an outer surface of the filter member are resiliently and watertightly in contact with one another.

3. The gas sensor unit as claimed in claim 1, wherein the filter member comprises a material which is water repellent and gas permeable at least in a direction of an axis of the communicating hole, said filter member having a main body and a surrounding outer peripheral surface, and the enclosing member is resilient such that an inner wall surface of the communicating hole is in close contact with the outer peripheral surface of the filter member.

4. The gas sensor unit as claimed in claim 3, wherein the inner wall surface of the communicating hole of the enclosing member includes an annular protruding portion protruding inwardly and being in close contact with a portion of the close contact portion of the filter member.

5. The gas sensor unit as claimed in claim 2, wherein the enclosing member includes a holding portion for holding the filter member in the communicating hole.

6. The gas sensor unit as claimed in claim 2, wherein the sensor cap includes a lead wire connecting to the cap terminal for transmitting the output signal to the external device, and the filter member includes an inserting hole which extends through and along an axis of the communicating hole and in which the lead wire is watertightly held.

7. The gas sensor unit as claimed in claim 6, wherein the filter member includes the close contact portion provided at an outer peripheral surface of the filter member and a crimping portion provided at a position different from the close contact portion in the direction of the axis and having a smaller outer diameter than that of the close contact portion,
wherein the sensor cap further includes a crimping member which crimps around the crimping portion of the filter member so that the lead wire is watertightly held in the inserting hole.

8. The gas sensor unit as claimed in claim 1, wherein the communicating hole includes a plurality of openings which are provided between the filter member and the space outside the gas sensor unit, and the filter member is positioned out of sight from outside the gas sensor unit through any of the plurality of openings.

9. The gas sensor unit as claimed in claim 1, comprising means for introducing a reference gas into the internal space from outside the sensor cap through the communicating hole, and a vent passage for introducing the reference gas to the gas detecting element provided between the filter member and the gas detecting element.

10. The gas sensor unit as claimed in claim 9, wherein when a direction of movement of the gas sensor when the sensor cap and the gas sensor are assembled is taken as a first moving direction, the cap terminal includes an inner vent passage extending in the first moving direction which is a part of the vent passage and an end portion provided on a side opposite the gas sensor in the first moving direction, and the end portion includes a contact portion abutting an inner surface of the enclosing member in the first moving direction and a non-contact portion spaced apart from the inner surface of the enclosing member so that the reference gas is introduced into the inner vent passage through a gap between the non-contact portion of the cap terminal and the inner surface of the enclosing member.

11. The gas sensor unit as claimed in claim 1, wherein the gas sensor further includes a cylindrical insulating member surrounding said sensor terminal, and wherein said cap terminal includes an inner tubular portion which is inserted into said cylindrical insulating member of the gas sensor and connected to the sensor terminal.

12. A sensor cap adapted for fitting to a gas sensor including a gas detecting element, an electrode provided on the gas detecting element and a sensor terminal connected to the electrode for transmitting an output signal from the gas detecting element to an external device, the sensor cap comprising:
a cap terminal for electrically connecting to the sensor terminal, said cap terminal being adapted to resiliently connect to the sensor terminal so that the gas sensor and the sensor cap detachably fit one another;
an enclosing member for accommodating the cap terminal therein and adapted to define a cap terminal accommodating space for forming an internal space in cooperation with the gas sensor when the sensor cap is fitted to the gas sensor, the enclosing member having a communicating hole through which the cap terminal accommodating space is in communication with a space outside the sensor cap; and
a filter member closing the communicating hole gas-permeably and watertightly.

13. The sensor cap as claimed in claim 12, wherein at least one of the enclosing member and the filter member comprises a resilient material, and an inner wall surface of the communicating hole of the enclosing member and an outer surface of the filter member are resiliently and watertightly in contact with one another.

14. The sensor cap as claimed in claim 13, wherein the filter member comprises a material which is water repellent and gas permeable at least in a direction of an axis of the communicating hole, and includes a close contact portion provided at an outer peripheral surface of the filter, and the enclosing member is resilient such that an inner wall surface of the communicating hole is in close contact with the main body of the filter member.

15. The sensor cap as claimed in claim 14, wherein the inner wall surface of the communicating hole of the enclosing member includes an annular protruding portion protruding inwardly and in close contact with a portion of the close contact portion of the filter member.

16. The sensor cap as claimed in claim 13, wherein the enclosing member includes a holding portion for holding the filter member in the communicating hole.

17. The sensor cap as claimed in claim 13, further comprising: a lead wire connecting to the cap terminal for transmitting the output signal to the external device, wherein the filter member includes an inserting hole which extends through and along the axis of the communicating hole and in which the lead wire is watertightly held.

18. The sensor cap as claimed in claim 17, wherein the filter member includes the close contact portion provided at an outer peripheral surface of the filter member and a crimping portion provided at a position different from the close contact portion in the direction of the axis and having a smaller outer diameter than that of the close contact portion,
    wherein the sensor cap further includes a crimping member which crimps around the crimping portion of the filter member so that the lead wire is watertightly held in the inserting hole.

19. The sensor cap as claimed in claim 12, wherein the communicating hole includes a plurality of openings which are provided between the filter member and the space outside the sensor cap, and the filter member is positioned out of sight from outside the sensor cap through any of the plurality of openings.

20. The sensor cap as claimed in claim 12, wherein when a direction of movement of the gas sensor when the sensor cap and the gas sensor are assembled is taken as a first moving direction, the cap terminal includes an inner vent passage extending in the first moving direction and an end portion provided on a side opposite the gas sensor in the first moving direction, and the end portion includes a contact portion abutting an inner surface of the enclosing member in the first moving direction and a non-contact portion spaced apart from the inner surface of the enclosing member so that a reference gas introduced form outside the sensor cap through the communicating hole is further introduced into the inner vent passage through a gap between the non-contact portion of the cap terminal and the inner surface of the enclosing member.

21. The gas sensor unit as claimed in claim 1, wherein the enclosing member includes an inserting hole, which is separately provided from the communicating hole, and the sensor cap includes a lead wire inserted in the inserting hole, the lead wire connecting to the cap terminal for transmitting the output signal to an external device.

22. The sensor cap as claimed in claim 12, wherein the enclosing member includes an inserting hole, which is separately provided from the communication hole, and the sensor cap includes a lead wire inserted in the inserting hole, the lead wire connecting to the cap terminal for transmitting the output signal to an external device.

23. The gas sensor unit as claimed in claim 1, wherein the cap terminal includes a sensor connecting portion for electrically connecting to the sensor terminal, a core wire crimping portion electrically connecting to a core wire of the lead wire by crimping, and a filter crimping portion fixing the lead wire and the filter member by crimping.

24. The gas sensor unit as claimed in claim 23, wherein the filter member includes a smaller diameter portion and a larger diameter portion which has a larger diameter than the smaller diameter portion, wherein the smaller diameter portion is crimped by the filter crimping portion of the cap terminal.

25. The sensor cap as claimed in claim 12, wherein the cap terminal includes a sensor connecting portion for electrically connecting to the sensor terminal, a core wire crimping portion electrically connecting to a core wire of the lead wire by crimping, and a filter crimping portion fixing the lead wire and the filter member by crimping.

26. The sensor cap as claimed in claim 25, wherein the filter member includes a smaller diameter portion and a larger diameter portion which has a larger diameter than the smaller diameter portion, wherein the smaller diameter portion is crimped by the filter crimping portion of the cap terminal.

* * * * *